(12) United States Patent
Coy

(10) Patent No.: US 8,759,004 B2
(45) Date of Patent: Jun. 24, 2014

(54) COMPOUNDS AND METHODS FOR DETECTION OF CARCINOMAS AND THEIR PRECURSOR LESIONS

(76) Inventor: Johannes Coy, Dossenheim (DE)

( * ) Notice: Subject to any disclaimer, the term of this patent is extended or adjusted under 35 U.S.C. 154(b) by 692 days.

(21) Appl. No.: 11/927,274

(22) Filed: Oct. 29, 2007

(65) Prior Publication Data

US 2008/0234393 A1 Sep. 25, 2008

Related U.S. Application Data

(62) Division of application No. 10/539,233, filed as application No. PCT/EP03/51028 on Dec. 16, 2003, now abandoned.

(30) Foreign Application Priority Data

Dec. 18, 2002 (EP) .................................. 02102814

(51) Int. Cl.
| | | |
|---|---|---|
| G01N 33/53 | (2006.01) | |
| G01N 33/574 | (2006.01) | |
| G01N 33/573 | (2006.01) | |
| A61K 38/17 | (2006.01) | |
| C12N 9/22 | (2006.01) | |

(52) U.S. Cl.
CPC ........ *G01N 33/573* (2013.01); *G01N 33/57484* (2013.01); *A61K 38/1709* (2013.01); *C12N 9/22* (2013.01); *G01N 2333/922* (2013.01)
USPC ......................................... 435/7.1; 435/7.23

(58) Field of Classification Search
None
See application file for complete search history.

(56) References Cited

U.S. PATENT DOCUMENTS

| 2002/0052308 A1* | 5/2002 | Rosen et al. ................. 514/1 |
| 2003/0175753 A1* | 9/2003 | Shaughnessy et al. ........... 435/6 |
| 2006/0199179 A1* | 9/2006 | Nakamura et al. ............... 435/6 |

FOREIGN PATENT DOCUMENTS

| WO | WO 00/52204 | * | 2/2000 | ............... C12Q 1/68 |
| WO | WO 02/088345 A2 | * | 11/2002 | ............... C12N 9/22 |
| WO | WO 2004/055514 A1 | * | 7/2004 | ............. G01N 33/48 |

OTHER PUBLICATIONS

Taber's Cyclopedic Medical Dictionary (1985, F.A. Davis Company, Philadelphia, p. 274).*
Busken, C et al, (Digestive Disease Week Abstracts and Itinerary Planner, 2003, abstract No. 850).*
Kaiser (Science, 2006, 313: 1370).*
Greenbaum et al. (Genome Biology, 2003, vol. 4, Issue 9, pp. 117.1-117.8).*
Brennan et al. (J. Autoimmunity, 1989, 2 (suppl.): 177-186).*
Zimmer (Cell Motility and the Cytoskeleton, 1991. 20:325-337).*
Hell et al. (Laboratory Investigation, 1995, 73: 492-496).*
Fu et al. (EMBO J., 1996, 15:43982-4401.*
Vallejo et al. (Biochimie, 2000 82:1129-1133).*
Pollack et al (Nature Genetics, 1999, 23:41-46).*
Janeway et al. (Immunobiology 5, 2001, p. 100-101).*
Rudikoff et al. (Proc. Natl. Acad. Sci USA 1982 vol. 79: 1979-1983).*
Bowie et al. (Science, 247:1306-1310, 1990).*
Gussow et al. (Methods in Enzymology, 1991, 203:99-121).*
Wu et al. (J. Mol. Biol. (1999) 294, 151-162).*
Martin et al. (EMBO J. 13, 5303-09, 1994).*
Coleman et al. (Research in Immunology, 1994; 145(1): 33-36).*
Abaza et al. (Journal of Protein Chemistry, vol. 11, No. 5, 1992, pp. 433-444).*
Burgess et al (J of Cell Bio. 111:2129-2138, 1990).*
Los et al. (Biochemistry, 2000, 39:7365-7373).*
Grimm, Martin et al. "A biomarker based detection and characterization of carcinomas exploiting two fundamental biophysical mechanisms in mammalian cells" BMC Cancer 2013, 13:569, pp. 1-18, http://www.biomedcentral.com/1471-2407/13/569 Dept. of Oral and Maxillofacial Surgery, University Hospital Tuebingen, Osianderstr. 2-8, 72076, Tuebingen, Germany.
Igney, Frederik "Tumor Counterattack: Apoptose-vermittelte Immunsuppression durch Tumore" von der Fakultät für Geo- and Biowissenschaften der Universität Stuttgart zur Erlangung des akademischen Grades eines Doktors der Naturwissenschaften (Dr. rer. nat.) genehmigte Dissertation Deutsches Krebsforschungszentrum Heidelberg, Germany, 2002, pp. 1-112.
O'Connel, Joe et al. "New in vivo evidence confirms that tumor-expressed Fas ligand impairs immune responses to cancer by inducing apoptosis of anti-tumor immune effector cells"—1999 Nature America Inc., http://medicine.nature.com, Nature Medicine , vol. 5, No. 3, Mar. 1999, pp. 267-268, Dept.of Medicine, University Hospital and Dept. of Surgery, Mercy Hospital, Nat'l University of Ireland, Cork, Ireland.

* cited by examiner

*Primary Examiner* — Peter J Reddig
(74) *Attorney, Agent, or Firm* — Patent Central LLC; Stephan A. Pendorf

(57) ABSTRACT

The present invention relates to compounds and methods for detection and treatment of carcinomas and their precursor lesions. The invention provides DNase nucleic acids and polypeptides useful for the detection and treatment of carcinomas and their precursor lesions. The invention is more specifically related to a method for detection of carcinomas and their precursor lesions comprising the detection of the level and/or the subcellular localization of one or more DNase molecules in biological samples. Furthermore the present invention provides methods for early diagnosis, prognosis and monitoring of the disease course of carcinomas and their precursor lesions as well as for the treatment of said lesions.

6 Claims, 7 Drawing Sheets

SEQUENCE LISTING

```
<160> NUMBER OF SEQ ID NOS: 6

<210> SEQ ID NO 1
<211> LENGTH: 20
<212> TYPE: PRT
<213> ORGANISM: Homo sapiens

<400> SEQUENCE: 1

Arg Glu Leu Asn Arg Phe Asp Gly Ser Gly Pro Tyr Ser Thr Leu Ser
1               5                   10                  15

Ser Pro Gln Leu
            20

<210> SEQ ID NO 2
<211> LENGTH: 18
<212> TYPE: PRT
<213> ORGANISM: Homo sapiens

<400> SEQUENCE: 2

His Trp Val Ile Ala Asp Gly Glu Asp Thr Thr Val Arg Ala Ser Thr
1               5                   10                  15

His Cys

<210> SEQ ID NO 3
<211> LENGTH: 20
<212> TYPE: PRT
<213> ORGANISM: Homo sapiens

<400> SEQUENCE: 3

Cys Ala Ser Leu Thr Lys Lys Arg Leu Asp Lys Leu Glu Leu Arg Thr
1               5                   10                  15

Glu Pro Gly Phe
            20

<210> SEQ ID NO 4
<211> LENGTH: 17
<212> TYPE: PRT
<213> ORGANISM: Homo sapiens

<400> SEQUENCE: 4

Thr Tyr Asp Arg Val Val Leu His Gly Glu Arg Cys Arg Ser Leu Leu
```

-continued

```
1               5                  10                 15
His

<210> SEQ ID NO 5
<211> LENGTH: 16
<212> TYPE: PRT
<213> ORGANISM: Homo sapiens

<400> SEQUENCE: 5

Leu Thr Glu Glu Glu Ala Leu Asn Ile Ser Asp His Tyr Pro Val Glu
1               5                  10                 15

<210> SEQ ID NO 6
<211> LENGTH: 17
<212> TYPE: PRT
<213> ORGANISM: Homo sapiens

<400> SEQUENCE: 6

Val Leu Ser Ser Tyr Val Tyr Asn Asp Glu Asp Val Phe Ala Arg
1               5                  10                 15
Glu
```

COMPOUNDS AND METHODS FOR DETECTION OF CARCINOMAS AND THEIR PRECURSOR LESIONS

CROSS-REFERENCE TO RELATED APPLICATIONS

This application claims priority to and incorporates by reference European Application 02102814.7 filed Dec. 18, 2002, PCT application PCT/EP2003/051028 filed Dec. 16, 2003, and U.S. application Ser. No. 10/539,233 filed Jun. 16, 2005, now abandoned of which this application is a division.

SEQUENCE LISTING

The instant application contains a Sequence Listing which has been submitted in ASCII format via EFS-Web and is hereby incorporated by reference in its entirety. Said ASCII copy, created on Jan. 25, 2008, is named 4007-009-1-11927274-corrected-sequence.TXT and is 1,678 bytes in size.

BACKGROUND OF THE INVENTION

The present invention relates to compounds and methods for detection and treatment of carcinomas and their precursor lesions. The invention provides DNase nucleic acids and polypeptides useful for the detection and treatment of carcinomas and their precursor lesions. The invention is more specifically related to a method for detection of carcinomas and their precursor lesions comprising the detection of the level and/or the subcellular localization of one or more DNase molecules in biological samples. Furthermore the present invention provides methods for early diagnosis, prognosis and monitoring of the disease course of carcinomas and their precursor lesions as well as for the treatment of said lesions.

In most tumours there is a strong correlation between the patients outcome following initial therapy and the stage at which the disease has been diagnosed. So the earlier the cancer could be detected the better are the chances for the patient to survive. Thus sensitive testing methods are required for detecting the tumours in early stages or even in preliminary stages of the cancer such as precancerous stages or the precursors of malignant cancerous stages.

The most promising methods for early diagnosis of tumours are those involving molecular markers characteristic for tumours or characteristic for precursory stages of tumours.

Cancer being a quite heterogeneous disease, multiple regulators of the cell growth can be involved in the genesis of cancer. These regulatory elements of the cell cycle can be either positive regulators, named oncogenes when mutated, so that a transformed state is reached, or negative regulators, named tumour suppressor genes. The number of factors known to be involved in the regulation of the cell cycle and potentially being causative agents in the development of cancer exceeds 100 up to know and is still increasing.

The molecules being involved in the emergence of the cancerous state of a cell can be used to discriminate between cancer cells and normal tissue. Thus cancerous tissue can be detected by detecting molecules characteristic for the cancer cells. This turns out to be sophisticated due to the large number of molecules potentially being involved in causing cancer.

For improved diagnosis of tumours there is a need for new marker molecules for use in diagnosis of carcinomas and their precursor lesions, that enable for specific early detection and give the opportunity to treat the disorders at an early stage.

BRIEF SUMMARY OF THE INVENTION

The present invention provides DNase nucleic acids and polypeptides for the use in detection of carcinomas and their precursor lesions. According to the present invention these molecules may be used as molecular markers that allow for comprehensive detection of carcinomas and their precursor lesions as e.g. gastrointestinal tract lesions, respiratory tract lesions, etc. even at early stages.

Furthermore a method for the detection of carcinomas and their precursor lesions is provided.

BRIEF DESCRIPTION OF THE DRAWINGS

Embodiments in accordance with the present invention are best understood by reference to the following detailed description when read in conjunction with the accompanying drawings.

DETAILED DESCRIPTION OF THE INVENTION

Figure 1:
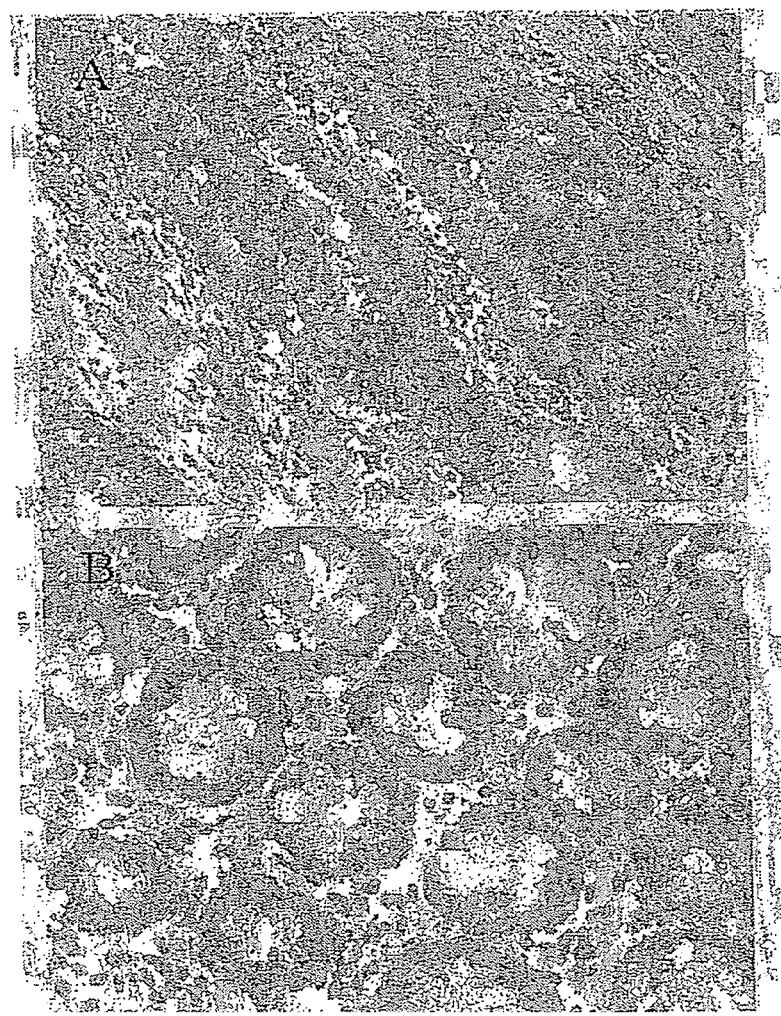
FIG. 1: Immunohistological specimen stained with antibodies directed against DNase X; A: colon carcinoma; B: corresponding normal tissue; the colon carcinoma specimen as well as the normal tissue has been subjected to an immunochemical staining reaction employing a primary antibody directed against DNase X; the figure shows nuclear positive staining for DNase X in the tumour cells; in normal tissue intraepithelial endocrine cells show immunoreactivity for DNase X in the cytoplasm; for experimental details see Example 1.
Figure 2:
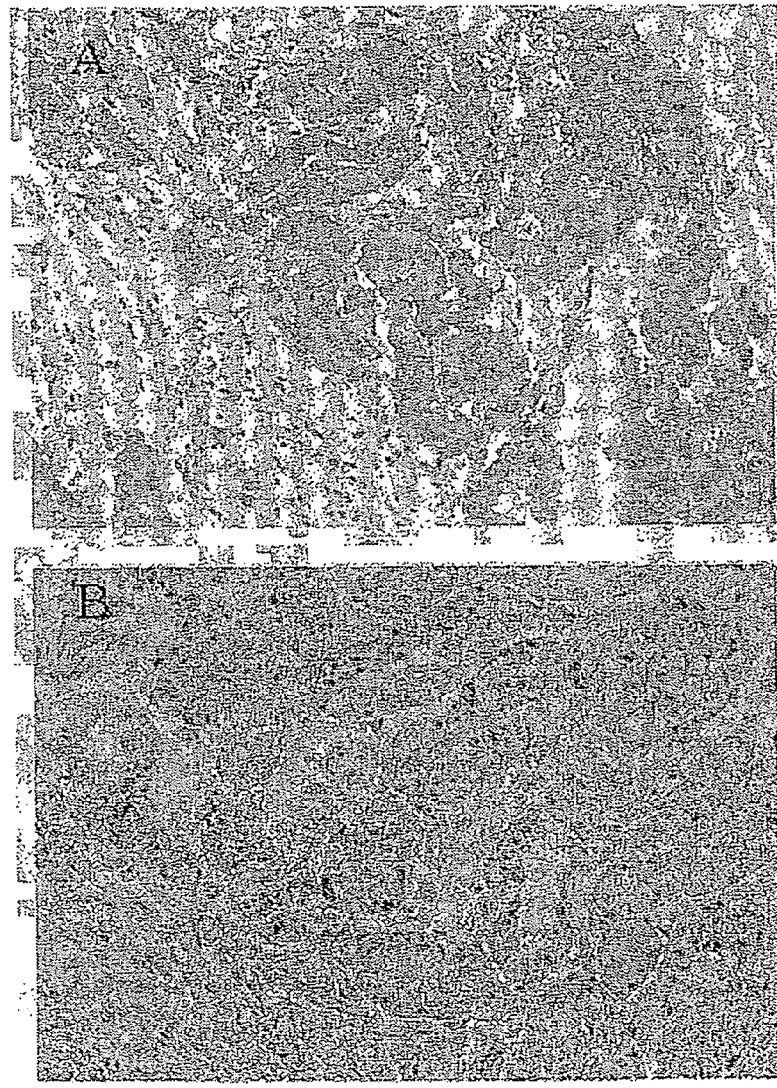
FIG. 2: Immunohistological specimen stained with antibodies directed against DNase X; A: gastric carcinoma; B: corresponding normal tissue; a gastric carcinoma specimen as well as corresponding normal tissue has been subjected to an immunochemical staining reaction employing a primary antibody directed against DNase X; the figure shows nuclear positive staining for DNase X in the tumour cells; in normal tissue glandular endocrine cells show immunoreactivity for DNase X in the cytoplasm; for experimental details see Example 1.
Figure 3:
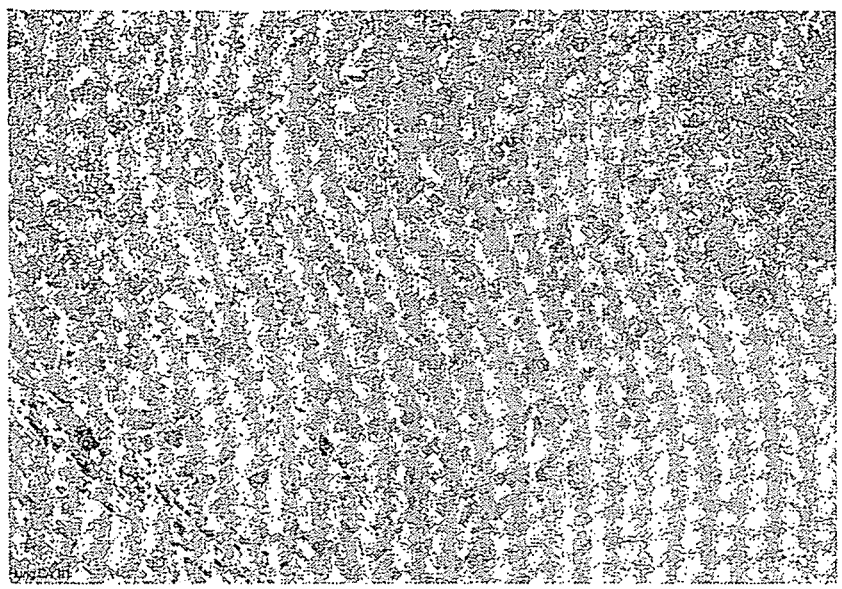
FIG. 3: Immunohistological specimen stained with antibodies directed against DNase X; a lung carcinoma specimen has been subjected to an immunochemical staining reaction employing a primary antibody directed against DNase X; the figure shows nuclear positive staining for DNase X in the tumour cells; for experimental details see Example 1.
Figure 4:
FIG. 4: Immunohistological specimen stained with antibodies directed against DNase X; A: adeno-carcinoma at the oesophago-gastrical junction; B: corresponding normal oesophageal tissue; an oesophageal carcinoma specimen as well as corresponding normal tissue has been subjected to an immunochemical staining reaction employing a primary antibody directed against DNase X; the figure shows nuclear positive staining for DNase X in the tumour cells; no staining is visible in the normal tissue; for experimental details see Example 1.
Figure 4:
Figure 5:
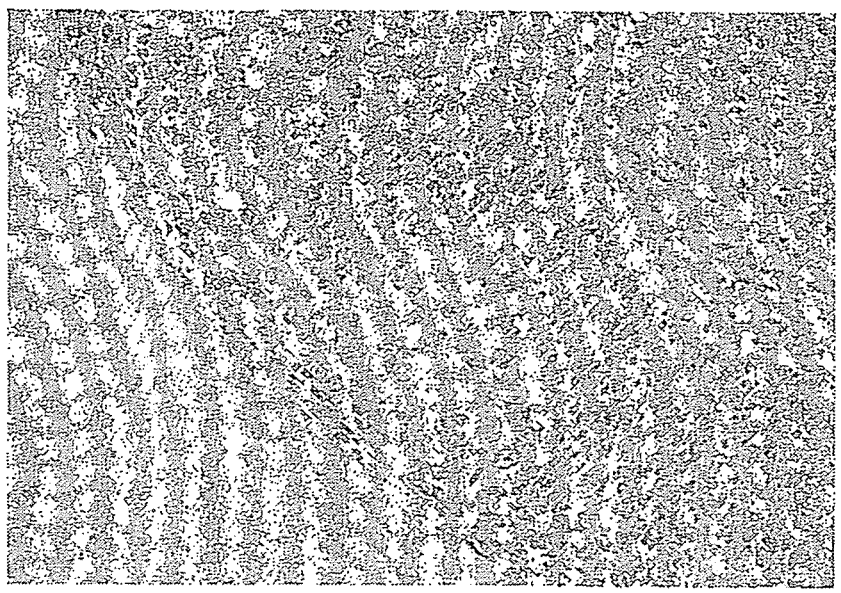
FIG. 5: Immunohistological specimen stained with antibodies directed against DNase X; a cervical dysplasia specimen (CINIII) has been subjected to an immunochemical staining reaction employing a primary antibody directed against DNase X; the figure shows nuclear positive staining for DNase X in the tumour cells; for experimental details see Example 1.
Figure 6:
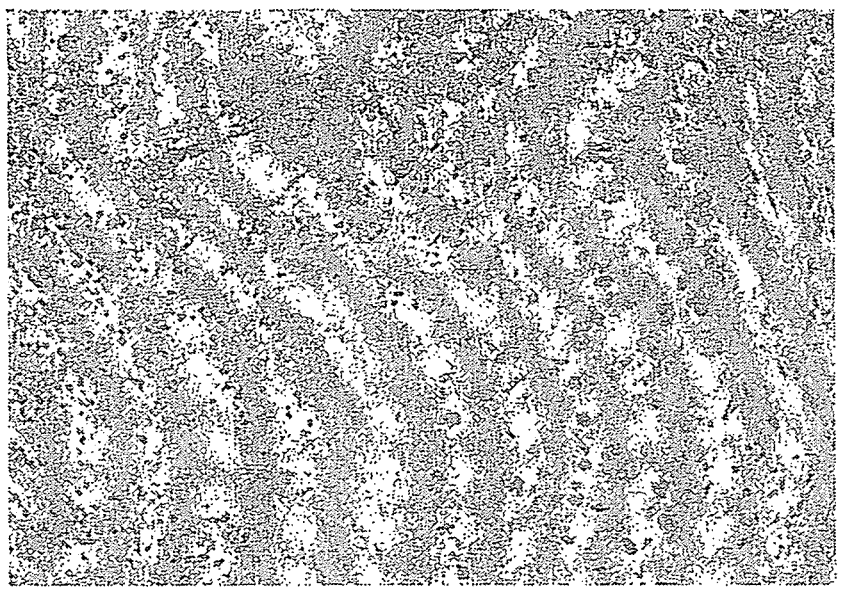
FIG. 6: Immunohistological specimen stained with antibodies directed against DNase X; a ductal carcinoma in situ has been subjected to an immunochemical staining reaction employing a primary antibody directed against DNase X; the figure shows nuclear positive staining for DNase X in the tumour cells; the neighbouring normal tissue shows no staining for DNase X; for experimental details see Example 1.

During the experiments leading to the present invention it could be shown, that DNase molecules may serve as molecular markers for the detection of carcinomas and their precursor lesions. Diagnostic value of DNase nucleic acid or polypeptides for detection of carcinomas and their precursor lesions is not published up to date.

Disclosure concerning the mutation of DNase in tumours may be found. Yet there is no hint as to the use of DNase molecules for the detection and diagnosis of carcinomas and their precursor lesions.

Investigation on the expression of DNase in carcinomas and their precursor lesions and in different stages of tumours elucidated its use for diagnostic and prognostic purposes. Thus the present invention is based on the inventors findings shown in the examples given below, that the level of expression of DNase nucleic acids as well as of the polypeptides encoded by these DNase nucleic acids in samples allows to diagnose and grade carcinomas and their precursor lesions such as e.g. gastrointestinal lesions, lesions of the respiratory tract, to predict the course of the disease and to follow up the disease after initial therapy.

The inventors could show, that in immunochemical procedures DNase may be detectable especially in specific subcellular regions such as e.g. in the nucleus. In the case of DNase X it could be shown, that differential staining patterns in immuno-histochemical procedures may depend on the respective binding agents employed in the experiments. It could be shown, that DNase X may be detected at equal levels in Western blot or ELISA assays from tumour and normal tissues. In contrast the same tissues render specific nuclear staining patterns for DNase X in tumour samples and lack staining in normal control samples. Furthermore the inventors found that detection of DNAse activity in body fluids may be used for the identification of individuals having cancers or cancer precursors.

This may be due to masking of the epitope, that is recognized by the employed antibody in normal tissue. In tumour tissue the epitope is unmasked especially in the cellular nucleus.

The present invention provides methods for the detection of carcinomas and their precursor lesions comprising the detection of one or more DNase molecules in a biological sample. The detection of DNase molecules in the course of the method according to the present invention may comprise the detection of the level of DNase molecules in biological samples, the detection of the presence or absence of DNase molecules in biological samples or the determination of the localization of DNase molecules e.g. in cells.

In one aspect the method according to the present invention is especially useful for early detection of disorders associated with abnormal cell proliferation such as e.g. colorectal lesions and for detection of disseminated tumour cells in the course of diagnosis of minimal residual disease. The method for detection of said carcinomas and their precursor lesions may comprise the detection of the (sub cellular) localization of DNase molecules, the detection of the presence or absence and/or the level of DNase molecules or the detection the accessibility (detectability) of specific epitopes of DNase molecules in biological samples. This method may e.g. employ minimally invasive or non-invasive procedures for obtaining the sample.

In another aspect of the present invention the above mentioned detection methods of DNase polypeptides and/or DNase nucleic acids may be used as molecular markers in the course of staging, assessment of prognosis, monitoring and the design of a strategy of tumour therapeutics.

The present invention furthermore provides DNase nucleic acids and polypeptides for use in the detection of carcinomas and their precursor lesions, such as e.g. colorectal lesions, lung cancer, gastric cancer, oesophageal cancer, breast cancer, cervical cancer etc.

The present invention also provides kits, such as diagnostic kits or research kits, for the detection of the DNase polynucleotides or DNase polypeptides or comprising DNase polynucleotides, DNase polypeptides or binding agents specifically binding to DNase polypeptides or polynucleotides for use in the detection of carcinomas and their precursor lesions.

One aspect of the present invention is a method for therapy of disorders associated with abnormal cell proliferation. In this aspect the inventive DNase polypeptides and/or polynucleotides may be administered to individuals suffering from said disorders in the course of immuno-therapy or gene-therapy.

One or more DNase nucleic acids and/or polypeptides may be used for therapy of carcinomas and their precursor lesions alone or in combination with other molecules.

Yet another aspect of the present invention are pharmaceutical compositions containing DNase polypeptides and/or DNase polynucleotides disclosed herein alone or combination with one or more other therapeutic or diagnostic agents and/or carrier or adjuvant substances.

It is yet another aspect of the present invention to provide methods for identification of molecules binding to the nucleic acids and polypeptides of the present invention as well as of activators and inhibitors of the expression of the genes of the present invention. Also a method for the identification of drug candidates for the therapy of carcinomas and their precursor lesions is provided.

DNase molecules for use in the context of the present invention comprise DNase I (AJ298844), DNase II (AB004574), DNase I-like 1 (DNase X) (NM_006730), DNase I-like 2 (AK098028), DNase I-like 3 (also called DNase gamma) (AF047354), caspase activated DNase (AB013918), DNase KIAA0218 (D86972), DNase II-like DNase (AF274571), DFF-45 (AF087573) and other known DNases.

DNase molecules as used in the context of the present invention may comprise nucleic acids, polynucleotides, proteins, polypeptides or peptides. On the level of nucleic acids the marker molecules may be DNA or RNA comprising genomic DNA, cDNA, and RNA such as mRNA or hnRNA.

Generally accessibility as used herein may comprise the localization of a particular region (the epitope) of a macromolecule on a surface, such that second or third molecules may get in contact or interaction to that region. Any method for the determination of the accessibility of a specific region of macromolecules may be employed in the methods according to the present invention. Such methods may e.g. comprise physical methods, such as e.g. spectroscopy, crystallography, etc., chemical methods, such as e.g. derivatization of functional groups in the macromolecules, crosslinking between neighbour regions in macromolecules etc. or application of binding agents e.g. in immunochemical procedures.

In certain embodiments accessibility of an epitope of a molecule may be determined by methods employing e.g. binding agents. In certain aspects of the present invention an epitope is said to be accessible, if binding agents specifically directed against said epitope may bind to and recognize the epitope in a sample. Inversely the epitope is said to be masked or inaccessible, if specific binding agents may not bind to the epitope.

Expression as used according to the present invention may comprise for example expression of proteins. The transcription to RNA and thus the level of mRNA may also be understood to be expression according to the present invention.

The expression of a compound is said to be significantly altered according to the present invention, if the level of expression differs by more than 30%. The alteration of the expression may comprise for example elevated expression or reduced expression of said compound. Another aspect of the altered expression may be an alteration in a way, that the compound is expressed under non wildtype circumstances. This may comprise, that the compound is for example expressed in situations, that naturally suppress the expression, or is not expressed in situations, that naturally induce the expression of the compound.

Alteration of the expression as used herein may also comprise an alteration in the transcription pattern of a gene. E.g. the alteration of the transcription pattern may comprise alternative splicing of the gene. The alterations in the transcription pattern may influence the polypeptides translated from the altered transcripts or may be restricted to untranslated regions. The alteration in the transcription pattern of a gene may comprise use of novel exons in the transcripts, deletions of exons in the transcripts or the variation in the ratios of different splicing variants in cells. Thus alterations in transcriptional patterns of genes as used herein may comprise the production of nucleic acids such as e.g. mRNA, cDNA etc. containing additional stretches of nucleic acid sequences compared to wild type nucleic acids occurring in control tissues.

Alternatively the nucleic acids produced by alternative splicing patterns may produce nucleic acids missing stretches of nucleic acid sequences present in wild type polynucleotides. The presence of additional stretches may occur simultaneously with the absence of original sequence-stretches in single transcripts. Alterations in the expression of genes as used in the context of the present invention may also comprise an alteration in the level of expression of splicing variants of genes. This may include increased or decreased expression of particular splicing variants as well as expression of variants not present in wild type tissue or the absence of expression of splicing variants present in wild type tissue. In one embodiment the alteration of the expression of the splicing variants may comprise the alteration of the ratios of different splicing variants in said tissue.

Nucleic acids as used in the context of the present invention are preferably polynucleotides or fragments thereof. Preferred polynucleotides comprise at least 20 consecutive nucleotides, preferably at least 30 consecutive nucleotides and more preferably at least 45 consecutive nucleotides, that are identical, share sequence homology or encode for identical, or homologous polypeptides, compared to the polypeptides associated with the proliferative disorders disclosed herein. The nucleic acids according to the present invention may also be complementary to any of said polynucleotides. Polynucleotides may for example include single-stranded (sense or antisense) or double-stranded molecules, and may be DNA (genomic, cDNA or synthetic) or RNA. RNA molecules comprise as well hnRNA (containing introns) as mRNA (not containing introns). According to the present invention the polynucleotides may also be linked to any other molecules, such as support materials or detection marker molecules, and may, but need not, contain additional coding or non-coding sequences.

The DNase polynucleotides for use in a method according to the present invention may be native sequences or variants thereof. The variants may contain one or more substitutions, additions, deletions and/or insertions such that the immunogenicity of the encoded polypeptide is not diminished, relative to the respective native DNase proteins. The variants show preferably 65-70%, more preferably at least 80% and most preferably at least 90% of sequence identity to the native nucleic acid molecules used in the methods according to the present invention. In one embodiment of the invention the variants show sequence identity of at least 65% to 99% or any value in between to the native DNase nucleic acids. In another embodiment of the invention the variants show sequence homologies of about 60, 65, 70, 75, 80, 85, 90, 95 or even 100%. Methods for determination of sequence similarity are known to those of skill in the art.

In one embodiment of the present invention a variant of DNase molecules may be employed, that is altered in a way, that interaction to natural ligands or binding partners is impaired.

One example for detecting the similarity of sequences can be carried out using the FastA and/or BlastN bioinformatics software accessible on the HUSAR server of the DKFZ Heidelberg.

Furthermore DNase nucleic acids for use in the methods according to the present invention are all polynucleotides, which hybridise to probes specific for the sequences disclosed herein under stringent conditions. Stringent conditions applied for the hybridisation reaction are known to those of ordinary skill in the art and may be applied as described in Sambrook et al. Molecular cloning: A Laboratory Manual, 2nd Edition, 1989.

The present invention also employs polynucleotides, that due to the degeneracy of the genetic code encode the DNase polypeptides natively encoded by the disclosed DNase nucleic acids while not showing the percentage of sequence homology as described above within the nucleic acid sequence. Such nucleic acids might arise by changing the codons present in the disclosed sequences by degenerate codons and so preparing a synthetic nucleic acid. In certain special embodiments the codons may be adjusted to the common codon usage of an appropriate transgenic host organism such as e.g. yeast, mice, rats, etc.

The DNase nucleotide sequences used according to the present invention may be joined to a variety of other nucleic acid sequences using the known recombinant DNA techniques. The sequences may for example be cloned into any of a variety of cloning vectors, such as plasmids, phagemids, lambda phage derivatives and cosmids. Furthermore vectors such as expression vectors, replication vectors, probe generation vectors and sequencing vectors may be joined with the sequences disclosed herein. Sequences of special interest, that could be cloned to the nucleic acids according to the present invention are for example non coding sequences and regulatory sequences including promoters, enhancers and terminators.

In certain embodiments of the present invention one or more of the nucleic acid sequences encoding DNase polypeptides may be joined. This may be especially useful for therapeutic purposes or for the expression of recombinant proteins.

In these embodiments 2, 3, 4, 5, 6, 7, 8, 9, 10 or even more different or even identical DNase nucleic acids may be joined together in one nucleic acid molecule.

In a preferred embodiment DNase polynucleotides may be formulated such, that they are able to enter mammalian cells and to be expressed in said cells. Such formulations are especially useful for therapeutic purposes. The expression of nucleic acid sequences in target cells may be achieved by any method known to those skilled in the art. The nucleic acids may for example be joined to elements that are apt to enable their expression in a host cell. Such elements may comprise promoters or enhancers, such as CMV-, SV40-, RSV-, metallothionein I- or polyhedrin-promoters respectively CMV- or SV40-enhancers. Possible methods for the expression are for example incorporation of the polynucleotides into a viral vector including adenovirus, adeno-associated virus, retrovirus, vaccinia virus or pox virus. Viral vectors for the purpose of expression of nucleic acids in mammalian host cells may comprise pcDNA3, pMSX, pKCR, pEFBOS, cDM8, pCEV4 etc. These techniques are known to those skilled in the art.

Other formulations for administration in therapeutic purposes include colloidal dispersion systems such as for example macromolecule complexes, microspheres, beads, micelles and liposomes.

Generally, by means of conventional molecular biological processes it is possible (see, e.g., Sambrook et al., supra) to introduce different mutations into the nucleic acid molecules of the invention. As a result the inventive tumour associated DNase polypeptides or polypeptides related thereto with possibly modified biological properties are synthesized. One possibility is the production of deletion mutants in which nucleic acid molecules are produced by continuous deletions from the 5'- or 3'-terminal of the coding DNA sequence and that lead to the synthesis of DNase polypeptides that are shortened accordingly. Another possibility is the introduction of single-point mutation at positions where a modification of the amino aid sequence influences, e.g., the proliferation specific properties. By this method muteins can be produced, for example, that possess a modified Km-value or that are no longer subject to the regulation mechanisms that normally exist in the cell, e.g. with regard to allosteric regulation or covalent modification, or altered binding-, dimerization-, inter- or intramolecule interaction properties. Such muteins might also be valuable as therapeutically useful agonists or antagonists of the DNase molecules used in the methods according to the present invention.

For the manipulation in prokaryotic cells by means of genetic engineering the DNase nucleic acid molecules of the invention or parts of these molecules can be introduced into plasmids allowing a mutagenesis or a modification of a sequence by recombination of DNA sequences. By means of conventional methods (cf. Sambrook et al., supra) bases can be exchanged and natural or synthetic sequences can be added. In order to link the DNA fragments with each other adapters or linkers can be added to the fragments. Furthermore, manipulations can be performed that provide suitable cleavage sites or that remove superfluous DNA or cleavage sites. If insertions, deletions or substitutions are possible, in vitro mutagenesis, primer repair, restriction or ligation can be performed. As analysis method usually sequence analysis, restriction analysis and other biochemical or molecular biological methods are used.

The DNase polypeptides encoded by the various variants of the DNase nucleic acid molecules of the invention show certain common characteristics, such as molecular weight, immunological reactivity or conformation or physical properties like the electrophoretic mobility, chromatographic behaviour, sedimentation coefficients, solubility, spectroscopic properties, stability, pH optimum, temperature optimum.

The invention furthermore employs vectors containing the inventive tumour associated DNase nucleic acid molecules. Preferably, they are plasmids, cosmids, viruses, bacteriophages and other vectors usually used in the field of genetic engineering. Vectors suitable for use in the present invention include, but are not limited to the T7-based dual expression vectors (expression in prokaryotes and in eucaryotes) for expression in mammalian cells and baculovirus-derived vectors for expression in insect cells. Preferably, the DNase nucleic acid molecule for use in the method according to the invention is operatively linked to the regulatory elements in the recombinant vector of the invention that guarantee the transcription and synthesis of an mRNA in prokaryotic and/or eucaryotic cells that can be translated. The nucleotide sequence to be transcribed can be operatively linked to a promoter like a T7, metallothionein I or polyhedrin promoter.

In a further embodiment, the present invention makes use of recombinant host cells transiently or stably containing DNase nucleic acid molecules. A host cell is understood to be an organism that is capable to take up in vitro recombinant DNA and, if the case may be, to synthesize the polypeptides encoded by the nucleic acid molecules of the invention. Preferably, these cells are prokaryotic or eucaryotic cells, for example mammalian cells, bacterial cells, plant cells, insect cells or yeast cells. The host cells for use in the invention are preferably characterized by the fact that the introduced DNase nucleic acid molecule either is heterologous with regard to the transformed cell, i.e. that it does not naturally occur in these cells, or is localized at a place in the genome different from that of the corresponding naturally occurring DNase sequence.

A further embodiment of the invention relates to the use of a polypeptide exhibiting a biological property of DNases and being encoded by the known DNase nucleic acid molecules.

These proteins or polypeptides may be produced by any suitable method including methods, whereby, e.g., a host cell is cultivated under conditions allowing the synthesis of the DNase polypeptide and the DNase polypeptide is subsequently isolated from the cultivated cells and/or the culture medium.

Isolation and purification of the recombinantly produced polypeptide may be carried out by conventional means including preparative chromatography and affinity and immunological separations using, e.g., an antibody directed against the inventive tumour associated marker proteins, or, e.g., can be substantially purified by the one-step method described in Smith and Johnson, Gene 67; 31-40 (1988).

The polypeptides for use in the present invention however, not only comprise recombinantly produced DNase polypeptides but include isolated naturally occurring DNase polypeptides, synthetically produced DNase polypeptides, or polypeptides produced by a combination of these methods. Means for preparing such polypeptides or related polypeptides are well understood in the art. These polypeptides are preferably in a substantially purified form.

The production of a DNase polypeptide for use in a method according to the present invention may for example be carried out in a cell free in vitro transcription and/or translation system. Such systems are known to those of ordinary skill in the art. One example may comprise an intro translation system as provided by Roche molecular Biochemicals' Rapid translation System.

DNase (poly) peptides as used in methods according to the present invention may comprise amino acid chains of any length, including full length proteins, wherein the amino acid residues are linked by covalent peptide bonds.

DNase peptides for use in the detection or treatment of carcinomas and their precursor lesions as disclosed in the context of the present invention shall comprise polypeptides of lengths of at least 4 amino acids. These DNase peptides may for example comprise 4 to 50 amino acids or any number of amino acids in between. In another embodiment of the present invention the peptides may comprise polypeptides with more than 50 amino acids. These DNase polypeptides for use in the methods of the present invention may for example comprise 50, 100, 500, 750, 1000 amino acids or any number of amino acids in between and may comprise proteins, or fragments thereof, and/or fusion- or chimeric proteins comprising on or more additional heterologous sequences. The additional sequences may be derived from the native DNase proteins or may be heterologous, and such sequences may (but need not) be immuno-reactive and/or antigenic. As detailed below, such polypeptides may be isolated from tumour tissue or prepared by synthetic or recombinant means.

As used herein, a polypeptide exhibiting biological properties of DNase peptides for use in the methods disclosed herein is understood to be a polypeptide having at least substantially the same immunogenic properties, i.e. is still capable of binding an antibody directed against a DNase polypeptide, e.g. comprises at least one immunogenic epitope of a DNase polypeptide.

Peptides for use in a method as disclosed herein may be e.g. immunogenic polypeptides. This requires, that the polypeptides may stimulate immune responses in host organisms either in the form the polypeptides adopt in their natural environment and/or especially in the form the polypeptides adopt after processing by the cellular antigen processing and presenting machinery.

Immunogenic portion as used above is a portion of a protein, that is recognized by a B-cell and/or Tcell surface antigen receptor. The immunogenic portions comprise at least 4 amino acid residues, at least 10 amino acid residues or at least 15 amino acid residues of the protein disclosed herein. In one embodiment of the present invention, particular domains of the protein, such as for example transmembrane domains or N-terminal leader sequences have been deleted.

The immunogenic portions according to the present invention react with antisera or specific antibodies in the same or nearly same intensity as the native full length proteins. The immunogenic portions are generally identified using the techniques well known in the art. Possible techniques are for example screening of the polypeptides for the ability to react with antigen-specific antibodies, antisera and/or T-cell lines or clones.

Suited immunogenic portions for DNase X may e.g. comprise the peptides:

| | | |
|---|---|---|
| 71-90: | RELNRFDGSGPYSTLSSPQL | (SEQ ID NO:1) |
| 207-24: | HWVIADGEDTTVRASTHC | (SEQ ID NO:2) |
| 187-206: | CASLTKKRLDKLELRTEPGF | (SEQ ID NO:3) |
| 225-241: | TYDRVVLHQERCRSLLH | (SEQ ID NO:4) |
| 254-269: | LTEEEALNISDHYPVE | (SEQ ID NO:5) |
| 110-126: | VLSSYVYNDEDDVFARE | (SEQ ID NO:6) |

These immunogenic sequences for DNase X shall be examples for immunogenic regions and shall not be construed to limit the scope of the present invention. For all DNases the immunogenic regions for use in a method according to the present invention may be determined by any suitable method. The methods for determining the respective immunogenic regions in the particular DNase molecules are known to those of skill in the art.

In certain embodiments of the present invention DNase polypeptides may comprise fusion or chimeric polypeptides containing sequences disclosed herein. Fusion proteins comprise the polypeptide according to the present invention together with any second and further polypeptides, such as e.g. one or more polypeptides of the same sequence or of another sequence. Heterologous polypeptides may comprise e.g. enzymes, receptor molecules, antigens, antigenic or immunogenic epitopes or fragments, antibodies or fragments thereof, signalling polypeptides or signal transducing polypeptides, labelled polypeptides etc. The immunogenic protein may for example be capable of eliciting a recall response. Examples of such proteins include tetanus, tuberculosis and hepatitis proteins (see, for example, Stoute et al. New Engl. J. Med., 336:86-91 (1997)). For use in pharmaceutical compositions fusion proteins comprising serum albumin or fragments thereof may be useful in certain embodiments of the present invention.

In one embodiment of the invention the fusion peptides may be constructed for enhanced detection or purification of the polypeptides, or of complexes of the DNase polypeptides with the respective immunological entities according to the present invention. For the purpose of purification tags, such as e.g. his-tags, myc-tags etc. may be added to the polypeptides. For the purpose of detection antigenic portions, enzymes, chromogenic sequences etc. may be fused to the polypeptides. The fusion proteins of the present invention may (but need not) include a linker peptide between the first and second polypeptides.

A peptide linker sequence may be employed to separate the first and the second polypeptides by a distance sufficient to ensure, that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes.

Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The DNase polypeptides for use in a method according to the present invention comprise also variants of the native DNase proteins. These variants may differ from the native protein in one or more alterations such as substitutions, deletions, additions and/or insertions. The immuno-reactivity of the variants according to the present invention is not substantially diminished compared to the native DNase proteins. In a preferred embodiment of the invention the immuno-reactivity is diminished less than 50% in a more preferred embodiment the immuno-reactivity is diminished less than 20% compared to the native polypeptides. In one embodiment the immuno-reactivity is diminished less than 5%, 10%, 15%, 20%, 25%, 30%, 35%, 40%, 45%, 50% or any value in between. In certain embodiments the immuno-reactivity of the variants is reduced by even more than 50%.

In one embodiment DNase variants may be deficient in one or more portions, such as for example N-terminal leader sequences, transmembrane domains or small N- and/or C-terminal sequences. The variants exhibit 60%, 65% or 70%, more preferably at least 75%, 80%, 85% or 90% and most preferably at least 92.5%, 95%, 97.5%, 98%, 98.5%, 99% or 99.5% identity to the DNase polypeptides disclosed according to the present invention.

The variants of the present invention are preferably conservative substitutions, so that the amino acids changed are substituted for amino acids with similar properties. The properties concerned may include polarity, charge, solubility, hydrophobicity, hydrophilicity and/or amphipathic nature of the amino acid residues. The variants disclosed herein may also comprise additional terminal leader sequences, linkers or sequences, which enable synthesis, purification or stability of the polypeptides in an easier or more comfortable way.

The DNase (poly)peptides for use in a method according to the present invention may be produced by any method known to those of skill in the art. E.g. the polypeptides may be isolated from cells or organisms expressing the polypeptides, may be produced recombinantly in recombinant host cells or may be synthesized chemically by the methods commonly applied for synthesis of polypeptides.

The term binding agent as used herein comprises a variety of substances such as oligopeptides, antibodies, peptidomimetic molecules comprising antigen binding oligopeptides, nucleic acids, carbohydrates, organic compounds, etc. Antibody according to the present invention preferably relates to antibodies which consist essentially of pooled monoclonal antibodies with different epitopic specificities, as well as distinct monoclonal antibody preparations. Monoclonal antibodies are made from an antigen containing fragments of the polypeptides of the invention by methods well known to those skilled in the art (see, e.g., Köhler et al., Nature 256 (1975), 495). As used herein, the term "antibody" (Ab) or "monoclonal antibody" (Mab) is meant to include intact molecules as well as antibody fragments (such as, for example, Fab and F(ab') 2 fragments) which are capable of specifically binding to protein. Fab and f(ab')$_2$ fragments lack the Fc fragment of intact antibody, clear more rapidly from the circulation, and may have less non-specific tissue binding than an intact antibody. (Wahl et al., J. Nucl. Med. 24: 316-325 (1983)). Thus, these fragments are preferred, as well as the products of a Fab or other immuno-globulin expression library. Moreover, antibodies of the present invention include chimerical, single chain, and humanized antibodies.

Binding agents used according to the present invention may for example be employed for the inhibition of the activity of the inventive DNase polypeptides. In this respect the term "binding agents" relates to agents specifically binding to the DNase polypeptides transcribed from the novel tumour associated nucleic acids and thus inhibiting the activity of said polypeptide. Such binding agents may for example comprise nucleic acids (DNA, RNA, PNA etc.), polypeptides (antibodies, receptors, antigenic fragments, oligopeptides), carbohydrates, lipids, organic or inorganic compounds (metalions, sulphur compounds, boranes, silicates, reducing agents, oxidizing agents). The binding agents may preferably interact with the polypeptide by binding to epitopes, that are essential for the biological activity. The interaction may be reversible or irreversibly. The binding may be non-covalent or even covalent binding to the polypeptide. Furthermore the binding agents may introduce alterations to the DNase polypeptide, that alter or diminish the biological activity of the inventive DNase polypeptide.

For certain purposes, e.g. diagnostic methods, the antibody or binding agent of the present invention may be detectably labelled, for example, with a radioisotope, a bioluminescent compound, a chemiluminescent compound, a fluorescent compound, a metal chelate, a biologically relevant binding structure such as biotin or digoxygenin or an enzyme. Furthermore any method suitable for the detection of the intermolecular interaction may be employed.

The antibody or antigen-binding agent is said to react specifically, if it reacts at a detectable level with a DNase protein as used in a method according to the present invention herein, and does not significantly react with other proteins. The antibodies according to the present invention may be monoclonal or polyclonal antibodies. Other molecules capable of binding specifically may be for example antigen-binding fragments of antibodies such as Fab fragments, RNA molecules or polypeptides. According to the present invention binding agents may be used isolated or in combination. By means of combination it is possible to achieve a higher degree of sensitivity.

In certain embodiments binding agents may exhibit selective specificities for the various DNase polypeptides that may be used in the methods according to the present invention. These binding agents may e.g. be defined by epitopic specificity. The specificity may e.g. be chosen in a way to ensure that only one polypeptide product of the DNase gene is recognized by the respective binding agent.

The antibodies or binding agents useful for the methods according to the present invention may comprise further binding sites for either therapeutic agents or other polypeptides or may be coupled to said therapeutic agents or polypeptides. Therapeutic agents may comprise drugs, toxins, radionuclides and derivatives thereof. The agents may be coupled to the binding agents either directly or indirectly for example by a linker or carrier group. The linker group may for example function in order to enable the coupling reaction between binding agent and therapeutic or other agent or the linker may act as a spacer between the distinct parts of the fusion molecule. The linker may also be cleavable under certain circumstances, so as to release the bound agent under said conditions. The therapeutic agents may be covalently coupled to carrier groups directly or via a linker group. The agent may also be non-covalently coupled to the carrier. Carriers that can be used according to the present invention are for example albumins, polypeptides, polysaccharides or liposomes.

The antibody used according to the present invention may be coupled to one or more agents. The multiple agents coupled to one antibody may be all of the same species or may be several different agents bound to one antibody.

The invention makes use of transgenic non-human animal such as transgenic mice, rats, hamsters, dogs, monkeys, rabbits, pigs, C. elegans and fish such as torpedo fish comprising a DNase nucleic acid molecule or vector of the invention, preferably wherein said DNase nucleic acid molecule or vector may be stably integrated into the genome of said non-human animal, preferably such that the presence of said DNase nucleic acid molecule or vector leads to the expression of the DNase polypeptide (or related polypeptide), or may otherwise be transiently expressed within the nonhuman animal. Said animal may have one or several copies of the same or different nucleic acid molecules encoding one or several forms of DNase polypeptide or mutant forms thereof. This animal has numerous utilities, including as a research model for the regulation of cell proliferation and differentiation and therefore, presents a novel and valuable animal in the development of therapies, treatment, etc. for diseases caused by deficiency or failure of the DNase protein involved in the development of cell proliferative disorders, e.g., tumours. Accordingly, in this instance, the nonhuman mammal is preferably a laboratory animal such as a mouse or rat.

In certain embodiments, the transgenic non-human animal further comprises at least one inactivated wild type allele of the corresponding gene encoding the inventive DNase polypeptide. This embodiment allows for example the study of the interaction of various mutant forms of DNase polypeptides. All the applications that have been herein before discussed with regard to a transgenic animal also apply to animals carrying two, three or more transgenes.

In the methods according to the present invention it might be also desirable to inactivate protein expression or function at a certain stage of development and/or life of the transgenic animal. This can be achieved by using, for example, tissue specific, developmental and/or cell regulated and/or inducible promoters which drive the expression of, e.g., an antisense or ribozyme directed against the RNA transcript encoding the inventive DNase encoding mRNA; see also supra. A suitable inducible system is for example tetracycline-regulated gene expression as described, e.g., by Gossen and Bujard (Proc. Natl. Acad. Sci. 89 USA (1992), 5547-5551) and Gossen et al. (Trends Biotech. 12 (1994), 58-62). Similar, the expression of the mutant inventive tumour associated protein may be controlled by such regulatory elements.

Furthermore, the invention in certain embodiments makes use of a transgenic mammalian cell which contains (preferably stably integrated into its genome or transiently introduced) a DNase nucleic acid molecule or part thereof, wherein the transcription and/or expression of the nucleic acid molecule or part thereof leads to reduction of the synthesis of a native DNase molecule. In a preferred embodiment, the reduction is achieved by an anti-sense, sense, ribozyme, co-suppression and/or dominant mutant effect. "Antisense" and "antisense nucleotides" means DNA or RNA constructs which block the expression of the naturally occurring gene product. In another embodiment the native nucleic acid sequence coding for the DNase polypeptide may be altered or substituted by a variant of said nucleic acid sequence, e.g. by means of recombination, thus rendering the DNase gene non functional. Thus an organism lacking the DNase activity may be produced according to knock out experiments.

In certain embodiments transgenic non-human animals with a reduced level of DNase protein may be useful. Techniques how to achieve this are well known to the person skilled in the art. These include, for example, the expression of antisense-RNA, ribozymes, of molecules which combine antisense and ribozyme functions and/or of molecules which provide for a co-suppression effect.

When using the antisense approach for reduction of the amount of the inventive tumour associated marker proteins in cells, the nucleic acid molecule encoding the antisense-RNA is preferably of homologous origin with respect to the animal species used for transformation. However, it is also possible to use nucleic acid molecules which display a high degree of homology to endogenously occurring nucleic acid molecules encoding a DNase protein. In this case the homology is preferably higher than 75%, 80% or 85%, particularly higher than 90%, 91%, 92%, 93% or 94% and still more preferably higher than 95%, 95.5%, 96%, 96.5%, 97%, 97.5%, 98%, 98.5%, 99% or 99.5%. The reduction of the synthesis of a DNase polypeptide for use in a method according to the invention in the transgenic mammalian cells can result in an alteration in, e.g., degradation of endogenous proteins. In transgenic animals comprising such cells this can lead to various physiological, developmental and/or morphological changes.

Thus, the present invention also makes use of transgenic non-human animals comprising the abovedescribed transgenic cells. These may show, for example, a deficiency in regulation of cell proliferation and/or differentiation compared to wild type animals due to the stable or transient presence of a foreign DNA resulting in at least one of the following features:

(a) disruption of (an) endogenous gene(s) encoding a DNase;
(b) expression of at least one antisense RNA and/or ribozyme against a transcript comprising a DNase nucleic acid;
(c) expression of a sense and/or non-translatable mRNA of a DNase nucleic acid;
(d) expression of an antibody directed against a DNase polypeptide;
(e) incorporation of a functional or non-functional copy of the regulatory sequence of a DNase; or
(f) incorporation of a recombinant DNase molecule or vector containing a DNase nucleic acid.

Methods for the production of a transgenic non-human animal for use in the present invention, preferably a transgenic mouse, are well known to the person skilled in the art. Such methods, e.g., comprise the introduction of a nucleic acid molecule or vector into a germ cell, an embryonic cell, stem cell or an egg or a cell derived thereof. The non-human animal can be used in accordance with a screening method described herein and may be a non-transgenic healthy animal, or may have a disorder, preferably a disorder caused by at least one mutation in a DNase protein and/or gene.

Such transgenic animals are well suited for, e.g., pharmacological studies of drugs in connection with mutant forms of the above described inventive tumour associated marker polypeptide. Production of transgenic embryos and screening of those can be performed, e.g., as described by A. L. Joyner Ed., Gene Targeting, A Practical Approach (1993), Oxford University Press. The DNA of the embryonal membranes of embryos can be analysed using, e.g., Southern blots with an appropriate probe, amplification techniques based on nucleic acids (e.g. PCR) etc.; see supra.

Another aspect of the present invention is a pharmaceutical composition for use in the treatment of carcinomas and their precursor lesions. The DNase polypeptides, DNase polynucleotides and DNase binding agents (esp. antibodies) used according to the present invention may be incorporated into pharmaceutical or immunogenic compositions.

The pharmaceutical compositions may be administered by any suitable way known to those of skill in the art. The administration may for example comprise injection, such as e.g., intracutaneous, intramuscular, intravenous or subcutaneous injection, intranasal administration for example by aspiration or oral administration. A suitable dosage to ensure the pharmaceutical benefit of the treatment should be chosen according the parameters, such as age, sex, body weight etc. of the patient, known to those of skill in the art.

The pharmaceutical compositions comprise said compounds and a physiologically acceptable carrier. The type of carrier to be employed in the pharmaceutical compositions of this invention, will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

A pharmaceutical composition for use in a method according to the present invention may for example contain DNA, that codes for one or more DNase polypeptides. The DNA may be administered in a way that allows the polypeptides to be generated in situ. Suitable expression systems are known to those skilled in the art. In another embodiment of the invention the DNase nucleic acids may be for example antisense constructs. Pharmaceutical compositions may also comprise DNase nucleic acid molecules expressible in a mammalian or human host system comprising a viral or other expression system for example an adenoviral vector system.

The DNase nucleic acid may also be administered as a naked nucleic acid. In this case appropriate physical delivery systems, which enhance the uptake of nucleic acid may be employed, such as coating the nucleic acid onto biodegradable beads, which are efficiently transported into the cells. Administration of naked nucleic acids may for example be useful for the purpose of transient expression within a host or host cell.

Alternatively the pharmaceutical compositions may comprise one or more polypeptides. The polypeptides incorporated into pharmaceutical compositions may be a DNase polypeptide. Optionally the DNase polypeptide may be administered in combination with one or more other known polypeptides such as for example enzymes, antibodies, regulatory factors, such as cyclins, cyclindependent kinases or CKIs, or toxins.

DNase polypeptides used in the present invention or fragments thereof, that comprise an immunogenic portion may be used in pharmaceutical compositions, wherein the polypeptide e.g. stimulates a response directed specifically against tumour cells in the patient. A patient may be afflicted with disease, or may be free of detectable disease. Accordingly, the DNase compounds may be used to treat cancer or to inhibit the development of cancer. The compounds may be administered either prior to or following a conventional treatment of tumours such as surgical removal of primary tumours, treatment by administration of radiotherapy, conventional chemotherapeutic methods or any other mode of treatment of the respective cancer or its precursors.

Immunogenic compositions may comprise one or more polypeptides and non-specific immuneresponse enhancers, wherein the non-specific immune response enhancer is capable of eliciting or enhancing an immune response to an exogenous antigen. Any suitable immune-response enhancer may be employed in the vaccines of this invention. For example, an adjuvant may be included. Most adjuvants contain a substance designed to protect the antigen from rapid catabolism, such as aluminium hydroxide or mineral oil, and a non-specific stimulator of immune response, such as lipid A, *Bordetella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Pharmaceutical compositions and vaccines may also contain other epitopes of tumour antigens, either incorporated into a fusion protein as described above (i.e., a single polypeptide that contains multiple epitopes) or present within a separate polypeptide.

The present invention further provides kits for use in e.g. research or diagnostic methods. Such kits may contain two or more components for performing a scientific or diagnostic assay. Components may be compounds, reagents, containers and/or equipment. One component may be an antibody or fragment thereof that specifically binds to a DNase polypeptide. Additionally the kit may contain reagents, buffers or others known in the art as necessary for performing the diagnostic assay. Alternatively the research kit or diagnostic kit may contain nucleotide probes or primers for the detection of DNASE DNA or RNA. Such a kit should contain appropriate additional reagents and buffers known in the art.

A kit according to present invention comprises:
a) reagents for the detection of the DNase marker molecules
b) the reagents and buffers commonly used for carrying out the detection reaction, such as buffers, detection-markers, carrier substances and others
d) a DNase marker sample for carrying out a positive control reaction.

The reagent for the detection of the DNase marker includes any agent capable of binding to the marker molecule. Such reagents may include proteins, polypeptides, nucleic acids, glycoproteins, proteoglycans, polysaccharides or lipids.

The sample for carrying out a positive control may comprise for example DNase nucleic acids in applicable form, such as solution or salt, DNase peptides in applicable form, tissue section samples or positive cells expressing the DNase molecules.

In a preferred embodiment of the invention the detection of the marker molecules is carried out on the level of polypeptides. In this embodiment the binding agents may be for example antibodies specific for DNase or fragments thereof.

In another embodiment of the test kit the detection of DNase is carried out on the nucleic acid level. In this embodiment of the invention the reagents for the detection may be for example nucleic acid probes or primers complementary to said DNase nucleic acids.

Carcinomas and their precursor lesions according to the present invention are disorders characterized by abnormal growth properties of cells or tissues compared to the growth properties of normal control cells or tissues. The growth of the cells or tissues may be for example abnormally accelerated or may be regulated abnormally. Abnormal regulation as used above may comprise any form of presence or absence of non wild-type responses of the cells or tissues to naturally occurring growth regulating influences. The abnormalities in growth of the cells or tissues may be for example neoplastic or hyperplastic. In one preferred embodiment of the invention the tumours are cancers or pre-cancerous conditions of the respiratory tract.

Disorders characterized by abnormal cell proliferation, as used in the context of the present invention, may comprise for example neoplasms such as benign and malignant tumours, carcinomas, sarcomas, leukemias, lymphomas or dysplasias. Tumours may comprise tumours of the head and the neck, tumours of the respiratory tract, tumours of the gastrointestinal tract, tumours of the urinary system, tumours of the reproductive system, tumours of the endocrine system, tumours of the central and peripheral nervous system, tumours of the skin and its appendages, tumours of the soft tissues and bones, tumours of the lymphopoietic and hematopoietic system, breast cancer, prostate cancer, gastrointestinal cancer, colorectal cancer, anogenital cancer etc.

In certain embodiments the disorders are for example adenomas or adenocarcinomas of the colon, disorders of the respiratory tract such as Squamous Cell Lung Carcinoma, Small Cell Lung Carcinoma, Adenocarcinoma of the Lung, Large Cell Lung Carcinoma, Adeno-Squamous Lung Carcinoma, Carcinoid Tumour of the Lung, Bronchial Gland Tumour or (malignant) Mesothelioma, anogenital cancer such as, cervical cancer, vulval cancer, vaginal cancer, cancer of the rectum, cancer of the anus and cancer of the penis.

A sample according to the method of the present invention is any sample, that may contain cells, tissues or body fluid. Furthermore any sample potentially containing the marker molecules to be detected may be a sample according to the present invention. Such samples are e.g. blood, plasma, serum, liquor, bone marrow, swabs, washes, secretions, transsudates, exudates, sputum, stool, urine, semen, cell- and tissue-samples, punctuates or biopsies.

Biopsies as used in the context of the present invention may comprise e.g. resection samples of tumours, tissue samples prepared by endoscopic means or needle biopsies. Furthermore any sample potentially containing the marker molecules to be detected may be a sample according to the present invention.

In one embodiment of the present invention samples comprise cells of the anogenital tract, of the respiratory tract, the gastrointestinal tract (esp. the colorectal tract) or of the skin and its appendages. In certain embodiments the cells may be cells of the uterine cervix, the vagina, the vulva, the penis, the anus, the rectum, the bronchic tree, the lung, the peritoneum, the peritoneal space, the naso-pharyngeal space, the oral cavity, the colon ascendens, the colon transversum, the colon descendens, the colon sigmoidum, the pancreas, the small intestine, the duodenum, the jejunum, the ileum, the caecum, the oesophagus, the stomach, the bile tree, the liver or the skin.

In certain embodiments of the present invention the sample may be a histological sample, a biopsy, or a cytological sample such as e.g. a smear, a swab, a wash, a body fluid containing cells (sputum, a secretion, saliva, etc.). In certain embodiments of the present invention the samples may comprise cells infected by papilloma virus. The samples may in certain embodiments comprise cervical smears, bronchioalveolar lavages, stool, samples obtained by endoscopic means such as e.g. gastroscopy, colonoscopy, bronchioscopy etc.

Preparation of a sample may comprise e.g. obtaining a sample of a tissue, of a body fluid, of cells from a patient. According to the present invention preparation of the sample may also comprise several steps of further preparations of the sample, such as preparation of dissections, preparation of cell suspensions, spreading or applying the cells to be examined onto microscopic slides, preparation of tissue arrays, isolation of polypeptides or nucleic acids, preparation of solid phase fixed peptides or nucleic acids or preparation of beads, membranes or slides to which the molecules to be determined are coupled covalently or non-covalently.

A sample for use in the method of the present invention may be obtained and prepared by any suitable procedure. The samples e.g. may comprise any samples of the content of the gastrointestinal tract (e.g. the stomach, the oesophagus or the bowel) of the respiratory tract (e.g. of the naso-pharyngeal space, the bronchus or the bronchioles), the anogenital tract (e.g. the vagina), the urogenital tract (e.g. the bladder or the urethra) the vascular system etc. The sample may be obtained by active excretion of the material by an individual, or may be may obtained in the course of a surgical, invasive or minimally invasive medical procedure. For example a stool sample, as used in the context of the present invention may be a sample of material contained in the lumen of the colon, which has been obtained by clysters, by colonoscopy, digitally from the rectum or may be obtained from a stool voided by a patient. A stool sample according to the present invention may, but need not contain cells or cell debris of colorectal origin. In one embodiment of the present invention the polypeptides used for the detection of the colorectal lesions are secreted proteins that may be detected in stool samples independent of the presence of cells or cell debris originating from a colorectal lesion within the sample. In one embodiment of the present invention the sample may comprise blood, lymph, lymph nodes, bone marrow etc. In another embodiment of the present invention the sample may comprise breast tissue, breast cells, nipple aspirates, ductal lavages or any sample containing cells or cell debris originating from the breast.

In certain embodiments of the present invention sample may refer to the respective material within the body of an individual such as the urine, the stool, the sputum etc. A sample in this context may be e.g. the content of the intestine of an individual in vivo. In this embodiment the (stool, urine, sputum, exudates, semen, secretion) sample need not to be separated from the patient to be subjected to the methods disclosed herein.

The method for preparation of the sample may comprise any method suitable for assuring accurate detection of the presence or absence of lesions associated with abnormal growth properties. In certain embodiments of the present invention the preparation of the samples may comprise e.g. picking any portion of a total samples (such as e.g. voided stool, excreted urine, obtained smear, wash, sputum) with any suitable means such as a spatula, a brush, a spoon, a tip, a cloth, a membrane, a capillary, a syringe, a needle or pin or the like. For example the sample preparation may comprise blotting of a portion of the sample (such as e.g. the surface of a stool) to a membrane, a foil, a plastic film or a cloth, picking a portion of the stool by means of a needle, syringe, capillary, spatula, spoon or the like. Sample preparation may in certain embodiments comprise swabs from the surface of solid or viscous samples (such as e.g. voided stool, certain secretions, etc) obtained by suitable means like a spatula, a brush, a tampon, a cloth, a porous or textile (cotton, cellulose, derivatized cellulose etc.) device or tip or any other suitable means.

In certain embodiments of the invention any random fraction of a sample may be suitable for performing the detection method disclosed herein. In certain other embodiments of the invention a sample may be prepared in a way to assure the presence of a representative portion of the total sample. Such representative portions may be e.g. obtained by the methods described in U.S. Pat. No. 6,303,304, which shall be incorporated herein by reference, for stool samples.

In certain special embodiments of the present invention the sample may be prepared as a monolayer or thin layer preparation of a cytological specimen. The respective methods for preparation of monolayer or thin-layer preparation in cytology are known to those of skill in the art. In one embodiment the preparation may e.g. comprise the ThinPrep™ technology. Other methods comprise conventional smears, or method employing suspensions of cells for preparation of the cytological specimens.

In certain embodiments of the present invention the procedure for enriching or purifying the polypeptides and/or polynucleotides of interest may be employed. Where the case may be, the identification of nucleic acids, proteins or peptides in complex samples, which comprise several nucleic acids, proteins or peptides, may be enhanced by a separation procedure of particular molecule species present in the sample. These purification processes may involve purification in the meaning of separating all nucleic acids, protein or peptide components of the sample from other components such as lipids, nucleic acids etc. In certain embodiments of the invention the purification may also involve the separation of nucleic acids and/or proteins or peptides of particular properties from other protein or peptide components within the mixture.

Generally the methods for purification of nucleic acids and polypeptides mentioned herein may be applied in the course of any detection procedure suitable for the detection of the DNase molecules of the present invention. Thus, as the case may be, any detection procedure for the detection of the marker molecules disclosed herein alone or combination with other marker molecules may comprise purification methods for nucleic acids and/or polypeptides as mentioned below. The purification process may be performed at any stage in the course of the total procedure e.g. before a detection or amplification reaction, subsequently to a detection or amplification reaction, in a single step reaction simultaneously to a detection or amplification reaction etc.

Separation of proteins and/or nucleic acids may be carried out by use of their physical, chemical or biological properties. Physical parameters used for separation may comprise charge, hydrophobicity, mass, volume, shape or any other physical parameter suitable for separating different protein or peptide species. Chemical parameters applicable in separation of proteins comprise the use of reactive groups such as hydroxyl-, sulfhydryl or any other reactive or non reactive structure suitable for the separation of proteins/peptides. Biological parameters which may be used for separating proteins may include enzymatic activity, molecular interactions such as e.g. binding of biological binding moieties, such as e.g. ligands or receptors, immunogenicity or any other biological property suitable for separating different proteins or peptides. With respect to nucleic acids biological parameter may especially pertain to hybridisation properties.

All parameters mentioned above may be used independently or in any combination suitable for separating and purifying nucleic acids, proteins and/or peptides. In one embodiment a complex sample may be separated by electrophoretic methods such as agarose gel electrophoresis, PAGE, SDS-PAGE, free flow electrophoresis, capillary electrophoresis, 2D-electrophoresis or any other electrophoretic method suitable for separating nucleic acids, proteins or peptides. In certain embodiments 2D-electrophoresis may be used such that the separation in the first dimension is based on charge (e.g. in a polyacrylamide gel under high voltage conditions) and the resulting separated proteins or peptides are separated by their mass (e.g. in a sodium dodecylsulfate polyacrylamide gel in a direction perpendicular to the first dimension). Alternatively the first dimension of separation of proteins or peptides may be achieved by isoelectric focussing of the molecules in a pH gradient under high voltage. In certain embodiments a pulsed field electrophoresis may be applied for the separation of the DNase molecules according to the present invention.

In certain further embodiments capillary electrophoresis may be used for the separation of complex mixtures. For example a capillary may be filled with a suitable separation medium such as e.g. polyacrylamide and the sample is put on one end (depending on the positioning of the capillary e.g. the top) of the capillary. Depending on buffer and gel conditions the proteins and or peptides in the sample may be separated by mass or charge, respectively.

Furthermore liquid chromatography may be applied for separating nucleic acids, proteins and/or peptides. Macromolecules such as nucleic acids, peptides and/or proteins may be separated according to their physical and or chemical behaviour and or biological behaviour and or combinations of these depending on the chromatographic media and or solvents used for chromatography. In one embodiment the complex mixture of proteins and/or peptides may be bound to a solid phase according to their charge and eluted separately by increasing salt concentrations. In one embodiment the complex mixture is separated by a solid phase according to their mass by using a solid phase with a defined pore size distribution where proteins and or peptides enlarge their flow rate by diffusion into the pores according to their mass.

In one embodiment the complex mixture of proteins and or peptides is separated by a solid phase according to their shape by using a solid phase with a defined pore shape and or pore size distribution where proteins and or peptides enlarge their flow rate by diffusion into the pores according to their shape. In one embodiment the complex mixture of proteins and or peptides is bound to a solid phase according to their hydrophobicity and eluted separately by applying a gradient of hydrophobic solvents. In one embodiment one or all chromatographic methods mentioned above combined in a manner which is suitable for separating complex mixtures of proteins and or peptides.

In certain embodiments two dimensional HPLC may be used for separation of nucleic acids, proteins and/or peptides. For example a separation by means of ion exchange columns may be applied in combination with a reversed phase column. The ion exchange column may for example be an anion or cation exchange column of a suitable strength for use in the method disclosed herein. Materials for use in these HPLC methods are known to those of ordinary skill in the art. In certain embodiments the eluates from the first column (eluted e.g. by means of increasing salt steps) may be loaded onto the reversed phase column. The reversed phase column may e.g. be eluted by an ascending gradient of an appropriate solvent (e.g. acetonitril).

In certain embodiments of the present invention a pretreatment of the separated macromolecules such as e.g. proteins or polypeptides may be applied prior to the detection reaction. Such procedures may for example employ reduction or oxidation of proteins or peptides, proteolytic cleavage, modification of the proteins or peptides, derivatization or application of protecting moieties to prevent reactive parts of the peptides from unwanted reactions. For example in certain embodiments sulfhydryl-groups may be prevented from oxidation. Generally a protein extract for use in the methods according to the present invention may but need not be digested with suitable enzymes such as trypsin or any other protease to prepare peptides suitable for detection.

In certain embodiments of the present invention one or more fragments may be present without subjecting the sample to any steps of sample preparation. This may be due to activity of (digestive) proteolytic enzymes within the sample such as e.g. in stool, in fluids of the gastrointestinal tract or in gastrointestinal secretions. The fragments may be detected by any means described herein. In one embodiment fragments may be detected in the course of a mass spectrometric analysis. Detection of the respective fragment peaks corresponding to the peptides derived from DNase may be especially useful for the detection of the presence or absence and/or the level of DNase proteins in samples.

In one embodiment of the present invention nucleic acids may but not need to be subjected to a purification process prior to a subsequent detection or amplification reaction. This may be desirable e.g. to further enhanced signal to noise ratios. Furthermore purification of nucleic acids may be also applied subsequently to amplification reaction as the case may be. Purification techniques for the purpose of purification of nucleic acids are known to those of ordinary skill in the art and comprise for example gel electrophoresis, chromatography, precipitation, ultra centrifugation etc. E.g. the nucleic acids may be purified using electrophoresis in a suitable solid, viscous or liquid medium, such as a gel made from substances known to those of skill in the art (agarose, polyacrylamid, starch etc.).

Alternatively nucleic acids may be purified using hybridisation of the nucleic acids to complementary or reverse-complementary nucleic acid probes (e.g. fixed to a solid phase such as beads, membranes, slides etc.) in the procedure of an affinity chromatography or other suitable capture formats. Additionally precipitation methods for precipitation of nucleic acids (e.g. using ethanol, isopropanol or other alcohol in appropriate concentration, trichloroacetic acid, or other suitable acids or any other agent suitable for precipitation of nucleic acids from solutions) may be applied for the purification as well as chromatographic methods, such as ion exchange chromatography, affinity chromatography etc. According to the present invention nucleic acids may be purified using ultra centrifugation techniques, such as density gradient centrifugation in e.g. an isokinetic or isopyknic manner or other suitable centrifugation techniques.

Generally a method for detection of the level of the marker molecules for use in the methods according to the present invention is any method, which is suited to detect and identify biological macromolecules such as nucleic acids, peptides and protein molecules in samples. In certain embodiments of the invention these methods may be methods exhibiting high sensitivity, so that even small amounts of molecules may be detected. In further embodiments of the present invention standard detection methods exhibiting suitable sensitivities may be employed. Any method may be employed such as e.g. those including detection reactions in solution, methods employing solid phase adsorbed or coupled agents, etc. The method may be in vitro methods or may be methods to be applied in vivo e.g. in the course of in vivo imaging procedures.

In certain embodiments more than one peptide derived from DNase polypeptides and/or polynucleotides will be determined in a detection procedure. The detection of the level of marker polypeptides or fragments thereof according to the present invention may be the detection of the level of single marker molecules in separated reaction mixtures as well as the detection of a combination of markers simultaneously.

Furthermore the detection of the DNase nucleic acids, polypeptides and/or polynucleotides as disclosed herein may be carried out in combination to one or more further detection reactions. These detection reaction may for example be reaction for determination of the presence of further suitable marker nucleic acids and/or polypeptides or of one or more nucleic acids marker molecules in the samples. Further marker molecules, that may be suitable for the detection of proliferative disorders in the course of a method as disclosed herein may comprise e.g. cyclins (Cyclin A, Cyclin, B, Cyclin E), cyclin-dependent kinase inhibitors (p13.5, p14, p15, p16, p18, p19, p21, p27 etc.), cyclin-dependent kinases (cdk2, cdk4, cdk6 etc.) cell cycle regulatory proteins (p14ARF, pRb, mdm2, p53), proliferation marker molecules (mcm2, mcm3, mcm4, mcm5, mcm6, mcm7, cdc2, cdc6, K167, Ki S2, PCNA, DNA polymerase delta, rF Kappa B, etc.), marker for viral infection (such as HBV, HPV (especially high risk HPV: 16, 18, 31, 33, 38, 44, 45, 58, 68, etc.), HIV etc.) or other tumour marker proteins or nucleic acids (e.g. her2neu, CEA, PSA etc.).

In certain embodiments the detection of the level of DNase molecules is performed indirectly by determination of the enzyme activity of the DNase. Enzyme activity may e.g. be determined by measuring degradation of enzyme substrates such as DNA. Methods for detection of DNase activities are known to those of skill in the art.

The detection of one or more molecular markers may be performed in a single reaction mixture or in two or separate reaction mixtures. The detection reactions for several marker molecules may for example be performed simultaneously in multi-well reaction vessels. The DNase nucleic acids and/or polypeptides disclosed herein may be detected using methods and/or reagents that specifically detect these molecules. Simultaneously one or more further markers may be detected using methods and/or reagents that specifically detect them. The detection procedure for each single marker may comprise one or more steps. In certain embodiments the detection procedure may comprise detection of the marker molecules by a primary detecting step followed by a further secondary detecting step making the result of the procedure available for quantitative and/or qualitative analysis. Examples of detection procedures involving multiple steps may e.g. comprise the use of primary and secondary and further binding agents.

In certain embodiments the detection procedure further may comprise a reporter reaction indicating the level of the inventive DNase polypeptides and/or nucleic acids. The reporter reaction may be for example a reaction producing a coloured compound, a bioluminescence or chemiluminescence reaction, a fluorescence reaction, generally a radiation emitting reaction, or a reaction involving a chemical binding reaction such as biotin binding or metal chelate binding.

In certain embodiments of the present invention procedures for the detection reaction according to the present invention may employ for example any immunological methods for detection of molecules, such as for example Western blot, dot blot, immuno-precipitation or immunological assays, such as ELISA, RIA, lateral flow assays etc.

In these embodiments determination of the (DNase) marker nucleic acids and/or polypeptides may for example be carried out in a reaction comprising a binding agent specific for the detection of the marker molecules. These binding agents may comprise for example nucleic acid probes, antibodies and antigen-binding fragments, bifunctional hybrid antibodies, peptidomimetics containing minimal antigen-binding epitopes etc. The binding agents may be used in many different detection techniques for example in southern-, northern-, western-blot, ELISA, lateral flow assay, (hybrid) capture assay, latex-agglutination, immuno-chromatographic strips or immuno-precipitation.

Generally binding agent based detection may be carried out as well in vitro as directly in situ for example in the course of an immuno-cytochemical staining reaction. Any other method suitable for determining the amount of particular polypeptides in solutions of biological samples, such as biochemical, chemical, physical or physico-chemical methods, may be used according to the present invention.

Methods for detection of methylation of nucleic acids are known to those of skill in the art and may comprise for example methods employing chemical pre-treatment of nucleic acids with e.g. sodium bisulphite, permanganate or hydrazine, and subsequent detection of the modification by means of specific restriction endonucleases or by means of specific probes e.g. in the course of an amplification reaction. The detection of methylation may furthermore be performed using methylation specific restriction endonucleases.

In one embodiment of the invention the detection of the level of marker molecules is carried out by detection of the level of nucleic acids coding for the marker molecules or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognising and binding to said nucleic acids. This method can be performed as well in vitro as directly in situ for example in the course of a detecting staining reaction. Another way of detecting the marker molecules in a sample on the level of nucleic acids performed in the method according to the present invention is an amplification reaction of nucleic acids, which can be carried out in a quantitative manner such as for example PCR, LCR or NASBA.

In certain embodiments of the present invention amplification of ribonucleic acids or of deoxyribonucleic acids may be applied to detect small amounts of DNase marker molecules or of small amounts of cells expressing DNase marker molecules in samples. This may be especially useful for the detection of dispersed tumour cells in samples, or for detection of DNase molecules, that have been dispersed to body fluids from tumour cells, that expressed these DNase molecules. Generally the detection of metastases, minimal residual disease or disseminated tumour cells in body samples may comprise a nucleic acid amplification reaction as mentioned above.

In the course of the detection of minimal residual disease generally detection of DNase molecules such as peptides, proteins, DNA or mRNA in blood samples or the detection of disseminated cells may be suitable. In the course of the detection of DNase molecules an amplification reaction (e.g. PCR, LCR, NASBA) may be employed. In the course of the detection of disseminated tumour cells may be separated from a body liquid and after lysing of the cells DNase molecules may be detected in the lysate. In certain embodiments of the present invention the detection of the dispersed tumour cells may be carried out in lymph node samples or in bone marrow samples to detect metastases or disseminated tumour cells, that have spread to the respective samples. It must be understood, that in the course of a detection of disseminated tumour cells any sample obtainable from an individual may be useful.

In one embodiment of the present invention the detection of a carcinomas or their precursor lesions or the detection of metastases or minimal residual disease in an individual may comprise the determination of the accessibility of a specific region of a DNase molecule in samples. This may comprise e.g. the detection of the capability of a site specific binding agent to react with DNase in a sample. Further more the detection of carcinomas and their precursor lesions as well as the detection of minimal residual disease or metastases may comprise the determination of the subcellular localization of DNase in cells.

Alternatively for the purpose of detection of disseminated tumour cells, metastases or minimal residual disease mass spectrometric detection of nucleic acids may be applied subsequently to amplification, or may be applied without amplification reaction.

In another embodiment of the invention the detection of the level of marker molecules is carried out by determining the level of expression of a protein. The determination of the marker molecules on the protein level may for example be carried out in a reaction comprising a binding agent specific for the detection of the marker molecules. These binding agents may comprise for example antibodies and antigen-binding fragments, bifunctional hybrid antibodies, peptidomimetics containing minimal antigen-binding epitopes etc. The binding agents may be used in many different detection techniques for example in western-blot, ELISA, lateral flow assay, latex-agglutination, immunochromatographic strips or immuno-precipitation. Generally binding agent based detection may be carried out as well in vitro as directly in situ for example in the course of an immuno-cytochemical staining reaction. Any other method suitable for determining the amount of particular polypeptides in solutions of biological samples, such as biochemical, chemical, physical or physico-chemical methods, can be used according to the present invention.

In certain embodiments of the present invention mass spectrometry may be used for detection of the DNase marker nucleic acids and/or polypeptides. Generally any type of mass spectrometry may be used in the method according to the present invention. The molecules to be analysed may be ionised by any suitable method. In one embodiment the ionisation method in the course of mass spectrometry may be a matrix assisted laser desorption ionisation, fast atom bombardment ionisation, electron spray ionisation or any other suitable method. Any technique known in the art for mass spectrometric resolution and detection of the generated ions may be used in the method according to the present invention. The mass spectrometric analysis may for example be performed by means of a time of flight analyser, may employ an ion trap, a quadrupole, a sector field analyser, a cyclotron etc.

The complete analysis including 2D-HPLC and mass spectrometric identification may for example be carried out on the ProteomeX-Workstation (ThermoFinnigan, San Jose, Calif., USA). The system includes a HPLC system comprising two HPLC pumps and an auto sampler which are connected to independently provide solvent to a strong cation exchange column and a reversed column. In the first step the tryptic digest is loaded onto the strong ion exchange column and washed using an appropriate solvent to remove any contaminations not suitable for further analysis. In increasing salt steps beginning with 1 mM ammonium chloride and ending at 900 mM ammonium chloride fractions of the proteolytic peptides are eluted from the strong cation exchange column and loaded onto the reversed phase column. Using the second HPLC pump the peptides on the reversed phase column are eluted by an ascending acetonitril gradient from 5 to 80% acetonitril in water after washing the bound peptides to remove access salt and conditioning the peptides for the subsequent mass spectrometric analysis. The peptides eluting from the reversed phase column are measured on line by use of an electrospray ionisation ion trap mass spectrometer (DECA LCQ, ThermoFinnigan, San Jose, Calif., USA) which enables the direct analysis and fragmentation of eluted peptides. Each reversed phase run is monitored continually by the ESI-MS and ESI-MS/MS spectra and saved for subsequent protein identification with the SEQUEST software package. SEQUEST uses peptide fragmentation mass spectra retrieved during the data dependent MS/MS process which generated fragment mass spectra of eluted peptides. The SEQUEST algorithm links experimentally derived fragment spectra with in silico generated fragment spectra from databases and enables correlation of the experimentally derived spectrum to the appropriate database record which identifies the peptide matching to this record.

The fragments detected during the MS analysis may be identified by comparison of these fragments to the data obtained from a database. Using appropriate algorithms proteins may be identified according to the fragment data obtained from the MS analysis.

In one embodiment peptide fragments obtainable by proteolytic cleavage of DNase proteins may be especially useful for the detection of DNase proteins in samples. Detection of the presence or the level of DNase proteins in samples may in one embodiment of the present invention comprise the detection of the presence or absence and/or the level of one or more proteolytic fragment peptides derived from DNase proteins in a sample. In one embodiment the detection may comprise the detection of the respective fragment peaks in a mass spectrum or in a complex pattern of different peptide fragment signals obtainable by a suitable analytical method.

In certain embodiments the separation of the proteins, subsequent analysis of the proteins and peptides and final identification of the proteins according to the detected mass spectra may be carried out in an assembled process.

Another technique suitable for peptide identification in complex samples uses 2D-Electrophoresis instead of 2D liquid chromatography. Gel spots stained with coomassie brilliant blue can be cut from the gel and digested using trypsin. The subsequent identification of both single peptides as well as the "mass fingerprint" of the digested protein can be performed using matrix assisted laser desorption and ionisation mass spectrometry or electrospray ionisation mass spectrometry.

For detection in mass spectrometry of nucleic acids purified nucleic acids may be subjected to amplification reactions. Suitable amplification reactions are known to those of ordinary skill in the art and may comprise DNA based amplification as well as RNA based amplification. Amplification reactions according to the present invention may comprise PCR, LCR, NASBA, etc. The amplification reaction may be performed using one or more specific primers. In one embodiment of the invention an amplification reaction comprises the amplification of a single nucleic acid. In another embodiment of the invention the amplification is carried out as a multiplex amplification reaction simultaneously amplifying a set of several nucleic acids.

In one embodiment of the present invention the amplified nucleic acids may be used for a subsequent primer extension reaction, with or without prior purification which gives rise to nucleic acid fragments of 10 to about 50 bp length.

In certain embodiments of the present invention immunological entities directed against DNase may be detected. This detection reaction may be carried out in the course of detection of disorders associated with the expression of DNase molecules or in the course of a immuno-therapy for determination of the immuno-status of an individual or for monitoring of the effect of an immunization or vaccination therapy.

In one embodiment of the invention the detection of the level of immunological entities specific for DNase peptides is carried out on the level of antibodies. The method for detection of disorders according to the present invention thus may employ the detection of immunological entities directed against one single peptide or the detection of a set of immunological entities. The use of a multiplicity of potential peptides raises the probability to detect the presence of a particular disorder, and may furthermore give additional information useful in stratification of a disorder, in monitoring the disease course or in assessment of prognosis concerning the disease course.

Immunological entities as used in the context of the present invention shall comprise any components of the mammalian immune system, that are able to specifically react with an antigenic epitope. Such immunological entities may comprise for example antibodies, all immuno-globulins, such as e.g. IgG, IgM, IgA, IgE, IgD, specific CD8+ T-cells or specific T-helper cells.

In this embodiment the detection may be e.g. performed using the specific interaction between the respective DNase peptides with the antibodies. The determination of the presence or absence and/or the level of antibodies directed against DNase peptides in an individual may for example be carried out with recombinantly produced DNase peptides. The peptides can be used in many different detection techniques for example in western-blot, ELISA or immuno-precipitation. In one embodiment the detection of antibodies is carried out as antibody capture assay (Antibodies A laboratory Manual, Harlow, Ed. et al., Cold Spring Harbor Laboratory 1988).

In another embodiment of the invention the detection of the specific antibodies is carried out using monoclonal or polyclonal antibodies specifically recognizing the antigen binding epitope of the first antibodies. For this purpose the above mentioned immunological detection procedures may be applied. In a further embodiment chimeric antigens may be employed in the detection reaction. Such chimeric antigens may for example comprise fusion proteins combining the antigenic epitope of a tumour associated polypeptide, recognized by the antibody in question, fused to another antigen, that may be recognized by a detection antibody. The particular antigens within the chimeric polypeptide may be separated by a linker or spacer region.

Any other method for determining the amount of particular antibodies or immuno-globulins in biological samples can be used according to the present invention.

Generally the detection of the antibodies according to the present invention may be performed as well in vitro as directly in situ for example in the course of an immunohistochemical or immunocytochemical staining reaction.

In one embodiment of the present invention the immunological entities directed against DNase molecules may be detected in a skin test. In this testing format peptides of DNase may be introduced intradermally into the skin of individuals in vivo. The testing format is known to those of skill in the art from the so called TINE test or the SERO test stamp by Sero-Mérieux. In this test the presence of immunological entities directed against DNase molecules is diagnosed from a reaction of the individual visible e.g. as inflammation of the skin at the respective point of injection of the peptide. The evaluation thus relies on reddening of the skin and e.g. formation of reddish papules etc. on the skin. The test result may be dependent e.g. on the diameter of the reddening or the papules detectable after application of the antigens. The test result may be recorded e.g. by photodocumentation.

The peptides (also called in this context "antigens") applicable for the detection of immunological entities in individuals may be produced by any method known to those of ordinary skill in the art and may comprise for example chemical synthesis of the polypeptides (fmoc-synthesis or equivalent) or may be produced recombinantly in any suitable host. However it must be obeyed, that the peptides are free of immunogenic components other than the respective DNase derived peptides.

The amounts of peptides that must be applied in this testing format in order to render visible immuno-reaction ranges between 0.1 µg and 10 µg of the purified peptide. In certain embodiments 0.05 µg, 0.1 µg, 0.5 µg, 1 µg or 5 µg of the antigen or any value in between may be used per application. The antigens (peptides) are preferably applied as solution (whereas any other suitable format of application such as powder, aerosol or the like may be used according to the present invention as well). The solvent may be any medically acceptable solution being sterile and free of pyrogens, that does not cause inflammatory or immunogenic reaction, when applied in a testing format as used in the presented skin test.

Cells exhibiting specificity for a DNase antigen may be detected by any methods suitable for that purpose known to those of ordinary skill in the art. Methods may for example comprise proliferation assays, cytokine-ELISAs, ELISpot assays, intracellular FACS-staining, PCR-mediated identification of peptide-specific cytokine (or similar)-expressing cells, tetramer-staining, cytotoxicity assays and DTH-(delayed type hypersensitivity) reactions.

In case of proliferation-assays induction of peptide-specific T-cell proliferation may be measured by methods known to those of skill in the art. This can be achieved by simple counting of cells, by measuring incorporation of labelled nucleotides into cellular DNA or by measuring level and/or activity of cellular protein(s). Cytokine-ELISA may comprise identification of peptide-specific cytokine-secreting cells by measuring cytokine levels in supernatant. In the course of an ELISpot assay the number of peptide-specific cytokine (i.e. IFN-g)-secreting cells in a sample is determined. Similarly the intracellular FACS-staining identifies cytokine-expressing cells on the protein level. In contrast (real-time) PCR may be used for identification of peptide-specific cytokine (or similar) expressing cells on the transcript level. In the course of a tetramer-staining assay the label is a tetramer-molecule of recombinant MHC-class I molecules, loaded with specific peptide and coupled to a dye. The tetramer binds to the T-cell receptor. Cytotoxicity assays are a method for identification of cells, that can recognize and kill target cells in a peptide-specific manner. DTH-(delayed type hypersensitivity) reaction is based on the measuring of skin-reaction of vaccinated persons after intradermal (or similar) application of peptide(s).

The method for the detection of immunological entities as disclosed herein may be performed for the purpose of monitoring in the course of immuno-therapeutic treatments of individuals. In this respect the presence or absence and or the level of antibodies directed against an inventive peptide in an individual is determined. The determination of the level may be performed using the methods as se forth above. The detection may be performed at several consecutive points in time as to monitor the timely alteration of the level of the immunological entities. The determination may for example be performed daily, weekly, monthly, once a year, or in once in a decade or at any interval in between.

In one preferred embodiment of the invention the level of markers is significantly elevated compared to a non tumourous test sample. In this case the marker is over expressed in the sample. In another preferred embodiment of the present invention the level of the marker is lowered compared to a non tumourous test sample. In a third embodiment there is no detectable expression of the marker at all in the test sample unlike in a control sample. In yet another embodiment there is detectable level of non wild-type marker molecules. Non wild-type marker molecules may comprise any marker molecules that deviate in sequence or structure from the structure or sequence, that is functional in wild type tissue not affected by a cell proliferative disease. Wild type sequences or structures are the sequences or structures predominantly present in normal cells or tissues. In one preferred embodiment of the invention the level of particular splicing variants of the marker gene is altered in the test samples compared to the wild type tissue. This may lead to altered levels of splicing variants, new splicing variants, neo-peptides, altered ratios of different splicing variants of genes.

The detection procedure according to the present invention may furthermore comprise a cytochemical staining procedure rendering a chromogenic or fluorescent staining of cells or cell compartments. Such staining procedures are known to those of skill in the art and may for example comprise e.g. staining for acidophilic or basophilic structures, of sub cellular regions (e.g. the nucleus, the mitochondria, the Golgi, the cytoplasm etc.), of specific molecules (the chromosomes, of lipids, of glycoproteins, of polysaccharides etc.) in the cytological specimens. Fluorescence dyes such as DAPI, Quinacrin, Chromomycin, etc. may be employed. Furthermore chromogenic dyes such as Azan, Acridin-orange, Hematoxylin, Eosin, Sudan-red, Thiazin-stains (Toluidin-blue, Thionin) may be applied. In other embodiments staining procedures such as Pap-staining, Giemsa-staining, Hematoxylin-Eosin staining, van-Gieson staining, Schiff-staining (using Schiff reagent), Feulgen staining, staining procedures employing precipitation of metals (such as e.g. of silver in staining procedures employing Silver Nitrate) or insoluble stains such as e.g. of Turnbulls-blue (or other insoluble metal cyanides), etc. may be used in the course of a method as disclosed herein. It must be understood, that the named dyes and staining methods shall be examples for the applicable methods and that any other method known in the art may be applied to a method as disclosed herein.

The staining procedures may produce chromogenic stains for light microscopic inspection or fluorescent stains for inspection under fluorescence microscopic conditions. In another embodiment of the present invention radiation emitting procedures, procedures employing substances impairing the transmission of radiation or other contrast media for imaging of the cytological conditions in a sample (e.g. the generation of optical impression by means such as (micro-) autoradiographic or (micro-)radiographic picture generation) may be of use for a method according to the present invention.

All the staining and imaging procedures may be used for analysis not only in microscopic procedures but also in automated analysis procedures such flow cytometry, automated microscopic (computerized or computer aided) analysis or any other method for analysis of stained cytological specimens.

The analysis of the staining or imaging results of the different procedures may be performed in a single analysis step or in different subsequent steps. E.g. the light microscopic inspection of a specimen may be performed before or after fluorescence microscopic inspection of the specimen. In Fluorescence microscopy the analysis of different stains with different excitation wavelengths may be analyses simultaneous or subsequently. Other imaging methods may be employed simultaneously or subsequently to the named procedures.

There may be various circumstances, under which combinations of different staining methods will be suitable. E.g. in cases, where no satisfying cytological staining results may be achieved by immunochemical staining the additional application of general cytological staining techniques may be suitable.

In certain embodiments of the present invention the method for detection of the marker molecules in samples may be performed in an automated manner. The automation of the method may be achieved by automated staining and analysis of histological or cytological specimens on a solid surface by microscopic means. In another embodiment the automation may comprise a flow cytometric analysis of the staining of cells in solution.

In one preferred embodiment the detection of tissues expressing DNase gene products is carried out in form of molecular imaging procedures. The respective procedures are known to those of ordinary skill in the art. Imaging methods for use in the context of the present invention may for example comprise MRI, SPECT, PET and other methods suitable for in vivo imaging.

In one embodiment the method may be based on the enzymatic conversion of inert or labelled compounds to molecules detectable in the course of molecular imaging methods by the marker molecules. In another embodiment the molecular imaging method may be based on the use of compounds carrying a suitable label for in vivo molecular imaging, such as radio isotopes, metal ions etc., specifically binding to marker molecules in vivo.

In a preferred embodiment of the invention these compounds are non-toxic compounds and may be eliminated from the circulation of organisms, such as humans, in a time span, that allows for performing the detection of label accumulated in tumour tissue over expressing the DNase marker gene. In another preferred embodiment of the invention compounds are used for molecular imaging, for which clearance from the circulation is not relevant for performing the molecular imaging reaction. This may be for example due to low background produced by the circulating molecules etc. The compounds for use in molecular imaging methods are administered in pharmaceutical acceptable form in compositions that may additionally comprise any other suitable substances, such as e.g. other diagnostically useful substances, therapeutically useful substances, carrier substances or the like.

The DNase molecules disclosed according to the present invention may be used for diagnosis, monitoring of the disease course and prognosis in cell proliferative disorders such as e.g. tumours.

Any methods for the detection of DNase molecules, of the accessibility of regions on DNase molecules or of immunological entities directed against DNase molecules according to the present invention may e.g. be useful in the course of diagnosis of carcinomas and their precursor lesions. Furthermore the methods for detection of DNase molecules or of immunological entities directed against DNase molecules may be used for the determination of an immuno-status of individuals e.g. in the course of immuno-therapy or vaccination procedures.

Diagnosis of carcinomas and their precursor lesions as used herein may for example comprise the detection of cells or tissues affected by abnormal growth. In one preferred embodiment diagnosis means the primary detection of a disease in an organism or sample.

According to the present invention the method for diagnosis carcinomas and their precursor lesions may be applied in routine screening tests for preventive aspects in order to detect said disease at an early stage of the onset of the disorder. For the purpose of early detection e.g. samples obtained by minimally invasive methods such as e.g. blood samples, stool samples, sputum samples, nipple aspirates, or samples obtained by methods comprising colonoscopy, bronchioscopy, bronchioalveolar-lavage, ductal-lavage etc. may be employed. The methods according to the present invention may be employed in the course of the detection of early stages of tumours and of precursory lesions of tumours or cancers.

In another preferred embodiment the diagnostic method may be used to determine the minimal residual disease of a tumour after primary therapy. In this respect the method of the invention may be applied to determine cells in body samples displaying abnormal expression of marker molecules according to the present invention, characteristic for tumours. Thus a spread of affected cells may be detected in body fluids.

In one embodiment of the invention the methods disclosed herein may be used for the detection and identification of metastases. The method may be applied either for detection of metastases in body tissues or organs by the detection methods described herein, or the metastases may be diagnosed with respect to prognosis and prediction of disease course.

Monitoring of the disease course may comprise determining the levels of marker molecules at different time points, comparing the levels at the different time points and assessing a diagnosis about the progression of the disease over the covered period of time. Thus monitoring may enable for assessment of prognosis and/or for design of an adequate therapy for a particular patient.

Monitoring or diagnosis as used in the context of the present invention may also comprise the detection of an immuno-status of individuals in the course of immuno therapy or vaccination therapy.

Prognosis of the disease course of a cell proliferative disorders such as e.g. tumours according to the present invention may comprise determining the level of expression of one or more marker molecules, comparing the levels with data from subsequent studies in a database and prognosticating the disease course from said comparison. In a preferred embodiment the method may comprise the detection of the levels of a set of marker molecules, the distinct levels of which may characterize distinct stages in the course of the disease. In a further embodiment of the invention the combination of the levels of a combination of markers may be an indicator for the prognosis of the further disease course and may build the basis for design of an adequate therapy.

Another aspect of the present invention is to provide a method for therapy and/or vaccination. According to the present invention a therapy of cell proliferative disorders can be carried out using the inventive DNase polypeptides and/or polynucleotides. The therapy may be for example immuno-therapy or somatic gene therapy.

The inventive DNase polypeptides and/or polynucleotides may according to the present invention be used for vaccination against cell proliferative disorders. Vaccination according to the present invention may comprise administering an immunogenic compound to an individual for the purpose of stimulating an immune response directed against said immunogenic compound and thus immunizing said individual against said immunogenic compound. Stimulating an immune response may comprise inducing the production of antibodies against said compound as well as stimulating cytotoxic T-cells. For the purpose of vaccination the polypeptides, nucleic acids and binding agents according to the present invention may be administered in a physiological acceptable form. The composition to be administered to individuals may comprise one or more antigenic components, physiologically acceptable carrier substances or buffer solutions, immuno-stimulants and/or adjuvants. Adjuvants may comprise for example Freund's incomplete adjuvant or Freund's complete adjuvant or other adjuvants known to those of skill in the art.

The composition may be administered in any applicable way such as e.g. intravenous, subcutaneous, intramuscular etc. The dosage of the composition depends on the particular case and purpose of the vaccination. It has to be adapted to parameters by the individual treated such as age, weight, sex etc. Furthermore the type of the immune response to be elicited has to be taken into account. In general it may be preferable if an individual receives 100 µg-1 g of a polypeptide according to the present invention or 106-1012 MOI of a recombinant nucleic acid, containing a nucleic acid according to the present invention in a form that may be expressed in situ.

Individuals for the purpose of vaccination may be any organisms containing the inventive tumour associated polypeptides and/or polynucleotides and being able to get affected by cell proliferative disorders.

Vaccination of individuals may be favourable e.g. in the case of altered, non wild-type sequences or structure of marker molecules associated with cell proliferative disorders. In one embodiment of the invention vaccination may be applied in cases, where non-wild type quaternary structures of DNases appear in carcinomas and their precursor lesions, that are not present in wild type tissue.

Polypeptides disclosed herein may also be employed in adoptive immuno-therapy for the treatment of cancer. Adoptive immuno-therapy may be broadly classified into either active or passive immunotherapy.

In active immuno-therapy, treatment relies on the in vivo stimulation of the endogenous host immune system to react against tumours with the administration of immune response-modifying agents (for example, tumour vaccines, bacterial adjuvants, and/or cytokines).

In passive immuno-therapy, treatment involves the delivery of biologic reagents with established tumour-immune reactivity (such as effector cells or antibodies) that can directly or indirectly mediate anti-tumour effects and does not necessarily depend on an intact host immune system. Examples of effector cells include T lymphocytes (for example, CD8+ cytotoxic T-lymphocyte, CD4+ T-helper, tumour-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immuno-therapy.

The predominant method of procuring adequate numbers of T-cells for adoptive immuno-therapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immuno-reactive polypeptides described herein may be used to rapidly expand antigen-specific T cell cultures in order to generate sufficient number of cells for immuno-therapy. In particular, antigen-presenting cells, such as dendritic, macrophage or B-cells, may be pulsed with immuno-reactive polypeptides or transfected with a nucleic acid sequence(s), using standard techniques well known in the art. For example, antigen presenting cells may be transfected with a nucleic acid sequence, wherein said sequence contains a promoter region appropriate for increasing expression, and can be expressed as part of a recombinant virus or other expression system. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al., "Therapy With Cultured T Cells: Principles Revisited," Immunological Reviews, 157:177, 1997).

The DNase polypeptides used herein may also be employed to generate and/or isolate tumour reactive T-cells, which can then be administered to the patient. In one technique, antigen-specific Tcell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the DNase polypeptides used according to the invention may be employed to generate tumour reactive T-cell subsets by selective in vitro stimulation and expansion of autologous T-cells to provide antigen-specific T-cells which may be subsequently transferred to the patient as described, for example, by Chang et al. (Crit. Rev. Oncol. Hematol., 22(3), 213, 1996). Cells of the immune system, such as T-cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immuno-reactive polypeptides contained within a delivery vehicle, such as a microsphere, to provide antigen-specific T-cells. The population of tumour antigen-specific T-cells is then expanded using standard techniques and the cells are administered back to the patient.

In another embodiment, T-cell and/or antibody receptors specific for the polypeptides can be cloned, expanded, and transferred into other vectors or effector cells for use in adoptive immuno-therapy.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate Tcells to provide antigen-specific T-cells, which may, in turn, be administered to a patient. The use of peptide-pulsed dendritic cells to generate antigen-specific T-cells and the subsequent use of such antigen-specific T-cells to eradicate tumours in a murine model has been demonstrated by Cheever et al, Immunological Reviews, 157:177, 1997.

These carcinomas and their precursor lesions according to the present invention comprise conditions characterized by abnormal growth properties of cells or tissues compared to the growth properties of normal control cells or tissues. The growth of the cells or tissues may be for example abnormally accelerated or may be regulated abnormally. Abnormal regulation as used above may comprise any form of presence or absence of non wild-type responses of the cells or tissues to naturally occurring growth regulating influences. The abnormalities in growth of the cells or tissues may be for example neoplastic or hyperplastic.

Disorders characterized by abnormal cell proliferation, as used in the context of the present invention, may comprise for example neoplasms such as benign and malignant tumours, carcinomas, sarcomas, leukemias, lymphomas or dysplasias. Tumours may comprise tumours of the head and the neck, tumours of the respiratory tract, tumours of the gastrointestinal tract, tumours of the urinary system, tumours of the reproductive system, tumours of the endocrine system, tumours of the central and peripheral nervous system, tumours of the skin and its appendages, tumours of the soft tissues and bones, tumours of the lymphopoietic and hematopoietic system, breast cancer, colorectal cancer, gastrointestinal cancer, anogenital cancer etc.

In certain embodiments the disorders are for example adenomas or adenocarcinomas of the colon, disorders of the respiratory tract such as Squamous Cell Lung Carcinoma, Small Cell Lung Carcinoma, Adenocarcinoma of the Lung, Large Cell Lung Carcinoma, Adeno-Squamous Lung Carcinoma, Carcinoid Tumour of the Lung, Broncheal Gland Tumour or (malignant) Mesothelioma, anogenital cancer such as, cervical cancer, vulval cancer, vaginal cancer, cancer of the rectum, cancer of the anus and cancer of the penis. In one embodiment the disorders may be breast cancer.

Additionally, vectors expressing DNase nucleic acids may be introduced into stem cells taken from the patient and clonally propagated in vitro for autologous transplant back into the same patient.

Monoclonal antibodies directed against DNase molecules be used as therapeutic compounds in order to diminish or eliminate tumours in a method according to the present invention. The antibodies may be used on their own (for instance, to inhibit metastases) or coupled to one or more therapeutic agents. Suitable agents in this regard include radio nuclides, differentiation inducers, drugs, toxins, and derivatives thereof. Preferred radio nuclides include 90Y, 123I, 125I, 131I, 186Re, 188Re, 211At, and 212Bi. Preferred drugs include methotrexate, and pyrimidine and purine analogues. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

In one embodiment of the invention the therapy of carcinomas and their precursor lesions may comprise the administration of antisense construct or ribozymes. The methods for administration of ribozymes or antisense constructs are known to those of skill in the art. The administration may take place as administration of naked nucleic acids or as administration of nucleic acids that are suited for expression of the relevant active products in situ.

In another embodiment of the invention the treatment carcinomas and their precursor lesions may comprise the administration of binding agents directed against the DNase polypeptides. These binding agents may for example be coupled to other compounds such as toxins, enzymes, radioisotopes etc.

In another embodiment of the invention therapy of carcinomas and their precursor lesions may comprise the administration of antagonists or agonists of DNase polypeptides, of binding partners of the DNase polypeptides, of inhibitors or enhancers of the expression of the DNase polypeptides or of drugs identifiable by assays involving the measurement of the activity of the DNase polypeptides. The methods for identifying these substances are known to those of skill in the art.

An example for a method for identifying a binding partner of a DNase polypeptide (or related polypeptide) and/or polynucleotide may comprise:
(a) contacting the inventive DNase polypeptide of the invention with a compound to be screened; and
(b) determining whether the compound effects an activity of the polypeptide.

The DNase polypeptides may be used to screen for proteins or other compounds that bind to the inventive colorectal lesion associated polypeptides or for proteins or other compounds to which the inventive colorectal lesion associated polypeptide binds. The binding of the DNase polypeptide and the molecule may activate (agonist), increase, inhibit (antagonist), or decrease activity of the DNase polypeptide or the molecule bound. Examples of such molecules include antibodies, oligonucleotides, proteins (e.g., receptors), or small molecules.

In one embodiment, the molecule is closely related to the natural ligand of the DNase polypeptide, e.g., a fragment of the ligand, or a natural substrate, a ligand, a structural or functional mimetic; see, e.g., Coligan, Current Protocols in Immunology 1(2) (1991); Chapter 5. Similarly, the molecule can be closely related to a natural receptor to which the DNase might bind, or at least, a fragment of the receptor capable of being bound by the DNase polypeptide (e.g., active site). In either case, the molecule can be rationally designed using known techniques.

Preferably, the screening for these molecules involves producing appropriate cells which express the DNase polypeptide, either as a secreted protein or on the cell membrane. Preferred cells include cells from mammals, yeast, *Drosophila*, or *E. coli*. Cells expressing the inventive colorectal lesion associated polypeptide (or cell membrane containing the expressed polypeptide) are then preferably contacted with a test compound potentially containing the molecule to observe binding, stimulation, or inhibition of activity of DNase polypeptide.

The assay may simply test binding of a candidate compound to the DNase polypeptide, wherein binding is detected by a label, or in an assay involving competition with a labelled competitor. Further, the assay may test whether the candidate compound results in a signal generated by binding to the DNase polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing the DNase, measuring the DNase polypeptide/molecule activity or binding, and comparing the DNase polypeptide/molecule activity or binding to a standard.

Preferably, an ELISA assay can measure the DNase level or activity in a sample (e.g., biological sample) using a monoclonal or polyclonal antibody. The antibody can measure the DNase polypeptide level or activity by either binding, directly or indirectly, to the DNase polypeptide or by competing with the DNase polypeptide for a substrate. All of these above assays can be used to screen for diagnostic or prognostic markers and for therapeutic agents. The molecules discovered using these assays can be used to treat disease or to bring about a particular result in a patient (e.g., elimination of a epithelial tumour or stop of progression of tumour growth) by activating or inhibiting the DNase polypeptide molecules. Moreover, the assays can discover agents which may inhibit or enhance the production of the DNase pol-peptides from suitably manipulated cells or tissues.

Therefore, the invention includes a method of identifying compounds for use in treatment of carcinomas and their precursor lesions which bind to a DNase polypeptides comprising the steps of:
(a) incubating a candidate binding compound with a DNase polypeptide; and (b) determining if binding has occurred. Moreover, the invention includes a method of identifying activators/agonists or inhibitors/antagonists of the inventive colorectal lesion associated polypeptide for use in treatment of disorders characterized by abnormal cell proliferation comprising the steps of: (a) incubating a candidate compound with a DNase polypeptide; b) assaying a biological activity of the DNase (enzymatic activity or other), and (c) determining if a biological activity of the DNase polypeptide has been altered.

In a further embodiment, the present invention relates to method of identifying and obtaining a drug candidate for therapy of carcinomas and their precursor lesions comprising the steps of
a. contacting a DNase or a cell expressing said DNase polypeptide in the presence of components capable of providing a detectable signal in response
   to altered regulation of cell proliferation
   to altered activity of a DNase polypeptide
   to altered cell differentiation, with said drug candidate to be screened under conditions to allow protein degradation, and
b. detecting presence or absence of a signal or increase of the signal generated from DNase polypeptide activity, cell proliferation or differentiation, wherein the presence or increase of the signal is indicative for a putative drug.

Experiments using animals or isolated cells or cell lines may be used to examine the proliferative behaviour of cells or tissues in dependence DNase polypeptide action. The same procedures may be employed for the study of cell differentiation.

The drug candidate may be a single compound or a plurality of compounds. The term "plurality of compounds" in a method of the invention is to be understood as a plurality of substances which may or may not be identical.

Said compound or plurality of compounds may be chemically synthesized or microbiologically produced and/or comprised in, for example, samples, e.g., cell extracts from, e.g., plants, animals or micro organisms. Furthermore, said compound(s) may be known in the art but hitherto not known to be capable of suppressing or activating a DNase polypeptide. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994) and in the appended examples. The plurality of compounds may be, e.g., added to the reaction mixture, culture medium, injected into a cell or otherwise applied to the transgenic animal. The cell or tissue that may be employed in the method of the invention preferably is a host cell, mammalian cell or non-human transgenic animal of the invention described in the embodiments hereinbefore.

If a sample containing a compound or a plurality of compounds is identified in the method of the invention, then it is either possible to isolate the compound from the original sample identified as containing the compound capable of suppressing or activating a DNase polypeptide, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical.

Several methods are known to the person skilled in the art for producing and screening large libraries to identify compounds having specific affinity for a target. These methods include the phage display method in which randomised peptides are displayed from phage and screened by affinity chromatography to an immobilized receptor; see, e.g., WO 91/17271, WO 92/01047, U.S. Pat. No. 5,223,409.

In another approach, combinatorial libraries of polymers immobilized on a chip are synthesized using photolithography; see, e.g., U.S. Pat. No. 5,143,854, WO 90/15070 and WO 92/10092. The immobilized polymers are contacted with a labelled receptor and scanned for label to identify polymers binding to the receptor.

The synthesis and screening of peptide libraries on continuous cellulose membrane supports that can be used for identifying binding ligands of the DNase polypeptide and thus possible inhibitors and activators is described, for example, in Kramer, Methods Mol. Biol. 87 (1998), 25-39. This method can also be used, for example, for determining the binding sites and the recognition motifs in the DNase polypeptides. In like manner, the substrate specificity of the DnaK chaperon was determined and the contact sites between human interleukin-6 and its receptor; see Rudiger, EMBO J. 16 (1997), 1501-1507 and Weiergraber, FEBS Lett. 379 (1996), 122-126, respectively.

Furthermore, the above-mentioned methods can be used for the construction of binding super topes derived from the polypeptide of the invention. A similar approach was successfully described for peptide antigens of the anti-p24 (HIV-1) monoclonal antibody; see Kramer, Cell 91 (1997), 799-809. A general route to fingerprint analyses of peptide-antibody interactions using the clustered amino acid peptide library was described in Kramer, Mol. Immunol. 32 (1995), 459-465. In addition, antagonists of the DNase can be derived and identified from monoclonal antibodies that specifically react with the polypeptide of the invention in accordance with the methods as described in Doring, Mol. Immunol. 31 (1994), 1059-1067.

More recently, WO 98/25146 described further methods for screening libraries of complexes for compounds having a desired property, especially, the capacity to agonize, bind to, or antagonize a DNase polypeptide or its cellular receptor. The complexes in such libraries comprise a compound under test, a tag recording at least one step in synthesis of the compound, and a tether susceptible to modification by a reporter molecule. Modification of the tether is used to signify that a complex contains a compound having a desired property. The tag can be decoded to reveal at least one step in the synthesis of such a compound. Other methods for identifying compounds which interact with the DNase polypeptides or DNase nucleic acid molecules encoding such molecules are, for example, the in vitro screening with the phage display system as well as filter binding assays or "real time" measuring of interaction using, for example, the BIAcore apparatus (Pharmacia).

All these methods can be used in accordance with the present invention to identify activators/agonists and inhibitors/antagonists of the DNase polypeptide or related polypeptide for use in a method of the present invention.

Various sources for the basic structure of such an activator or inhibitor can be employed and comprise, for example, mimetic analogues of the polypeptide of the invention. Mimetic analogues of the DNase polypeptide of the invention or biologically active fragments thereof can be generated by, for example, substituting the amino acids that are expected to be essential for the biological activity with, e.g., stereo isomers, i.e. D-amino acids; see e.g., Tsukida, J. Med. Chem. 40 (1997), 3534 3541. Furthermore, in case fragments are used for the design of biologically active analogues promimetic components can be incorporated into a peptide to re-establish at least some of the conformational properties that may have been lost upon removal of part of the original polypeptide; see, e.g., Nachman, Regul. Pept. 57 (1995), 359-370.

Furthermore, the DNase polypeptide can be used to identify synthetic chemical peptide mimetics that bind to or can function as a ligand, substrate, binding partner or the receptor of the polypeptide of the invention as effectively as does the natural polypeptide; see, e.g., Engleman, J. Clin. Invest. 99 (1997), 2284-2292. For example, folding simulations and computer redesign of structural motifs of the polypeptide of the invention can be performed using appropriate computer programs (Olszewski, Proteins 25 (1996), 286-299; Hoffman, Comput. Appl. Biosci. 11 (1995), 675-679). Computer modelling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of the DNase polypeptides and their possible ligand or other interacting proteins by computer assistant searches for complementary peptide sequences (Fassina, Immunomethods 5 (1994), 114-120. Further appropriate computer systems for the design of protein and peptides are described in the prior art, for example in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991.

The results obtained from the above-described computer analysis can be used for, e.g., the preparation of peptide mimetics of the DNase protein or fragments thereof. Such pseudo-peptide analogues of the natural amino acid sequence of the protein may very efficiently mimic the parent protein (Benkirane, J. Biol. Chem. 271 (1996), 33218-33224). For example, incorporation of easily available achiral-amino acid residues into a protein of the invention or a fragment thereof results in the substitution of amide bonds by polymethylene units of an aliphatic chain, thereby providing a convenient strategy for constructing a peptide mimetic (Banerjee, Biopolymers 39 (1996), 769-777).

Superactive peptidomimetic analogues of small peptide hormones in other systems are described in the prior art (Zhang, Biochem. Biophys. Res. Commun. 224 (1996), 327-331). Appropriate peptide mimetics of the protein of the present invention can also be identified by the synthesis of peptide mimetic combinatorial libraries through successive amide alkylation and testing the resulting compounds, e.g., for their binding and immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715.

Furthermore, a three-dimensional and/or crystallographic structure of the DNase polypeptide can be used for the design of peptide mimetic inhibitors of the biological activity of the polypeptide of the invention (Rose, Biochemistry 35 (1996), 12933-12944; Rutenber, Bioorg. Med. Chem. 4 (1996), 1545-1558).

The structure-based design and synthesis of low-molecular-weight synthetic molecules that mimic the activity of the native biological polypeptide is further described in, e.g., Dowd, Nature Biotechnol. 16 (1998), 190-195; Kieber-Emmons, Current opinion Biotechnol. 8 (1997), 435-441; Moore, Proc. West Pharmacol. Soc. 40 (1997), 115-119; Mathews, Proc. West Pharmacol. Soc. 40 (1997), 121125; Mukhija, European J. Biochem. 254 (1998), 433-438.

It is also well known to the person skilled in the art, that it is possible to design, synthesize and evaluate mimetics of small organic compounds that, for example, can act as a substrate or ligand to the DNase pol-peptides used in the invention or the related polypeptide. For example, it has been described that D-glucose mimetics of hapalosin exhibited similar efficiency as hapalosin in antagonizing multidrug resistance assistance-associated protein in cytotoxicity; see Dinh, J. Med. Chem. 41 (1998), 981-987.

The DNase nucleic acid molecule can also serve as a target for activators and inhibitors. Activators may comprise, for example, proteins that bind to the mRNA of a gene encoding a DNase polypeptide, thereby stabilizing the native conformation of the mRNA and facilitating transcription and/or translation, e.g., in like manner as Tat protein acts on HIV-RNA. Furthermore, methods are described in the literature for identifying nucleic acid molecules such as an RNA fragment that mimics the structure of a defined or undefined target RNA molecule to which a compound binds inside of a cell resulting in retardation of cell growth or cell death; see, e.g., WO 98/18947 and references cited therein. These nucleic acid molecules can be used for identifying unknown compounds of pharmaceutical and/or agricultural interest, and for identifying unknown RNA targets for use in treating a disease. These methods and compositions can be used in screening for novel antibiotics, bacteriostatics, or modifications thereof or for identifying compounds useful to alter expression levels of proteins encoded by a nucleic acid molecule.

Alternatively, for example, the conformational structure of the RNA fragment which mimics the binding site can be employed in rational drug design to modify known antibiotics to make them bind more avidly to the target. One such methodology is nuclear magnetic resonance (NMR), which is useful to identify drug and RNA conformational structures. Still other methods are, for example, the drug design methods as described in WO 95/35367, U.S. Pat. No. 5,322,933, where the crystal structure of the RNA fragment can be deduced and computer programs are utilized to design novel binding compounds which can act as antibiotics.

Some genetic changes lead to altered protein conformational states. For example, some mutant the inventive colorectal lesion associated polypeptides may possess a tertiary structure that renders them far less capable of protein degradation. Restoring the normal or regulated conformation of mutated proteins is the most elegant and specific means to correct these molecular defects, although it may be difficult. Of particular interest in this regard is the consensus domain of the inventive colorectal lesion associated polypeptide.

The compounds which can be tested and identified according to a methods of the invention may be expression libraries, e.g., cDNA expression libraries, peptides, proteins, nucleic acids, antibodies, small organic compounds, hormones, peptidomimetics, PNAs or the like (Milner, Nature Medicine 1 (1995), 879-880; Hupp, Cell 83 (1995), 237-245; Gibbs, Cell 79 (1994), 193-198 and references cited supra). Furthermore, genes encoding a putative regulator of the DNase polypeptide and/or which exert their effects up- or downstream the DNase polypeptide may be identified using, for example, insertion mutagenesis using, for example, gene targeting vectors known in the art. Said compounds can also be functional derivatives or analogues of known inhibitors or activators. Such useful compounds can be for example transacting factors which bind to the inventive tumour associated polypeptide or regulatory sequences of the gene encoding it. Identification of transacting factors can be carried out using standard methods in the art (see, e.g., Sambrook, supra, and Ausubel, supra).

To determine whether a protein binds to the DNase protein itself or regulatory sequences, standard native gel-shift analyses can be carried out. In order to identify a transacting factor which binds to the protein or regulatory sequence, the protein or regulatory sequence can be used as an affinity reagent in standard protein purification methods, or as a probe for screening an expression library.

The identification of nucleic acid molecules which encode polypeptides which interact with the inventive DNase described above can also be achieved, for example, as described in Scofield (Science 274 (1996), 2063-2065) by use of the so-called yeast "two-hybrid system". In this system the polypeptide encoded by a nucleic acid molecule according to the invention or a smaller part thereof is linked to the DNA-binding domain of the GAL4 transcription factor. A yeast strain expressing this fusion polypeptide and comprising a lacZ reporter gene driven by an appropriate promoter, which is recognised by the GAL4 transcription factor, is transformed with a library of cDNAs which will express plant proteins or peptides thereof fused to an activation domain. Thus, if a peptide encoded by one of the cDNAs is able to interact with the fusion peptide comprising a peptide of a inventive DNase polypeptide, the complex is able to direct expression of the reporter gene. In this way the nucleic acid molecules according to the invention and the encoded peptide can be used to identify peptides and proteins interacting with the DNase protein. It is apparent to the person skilled in the art that this and similar systems may then further be exploited for the identification of inhibitors of the binding of DNase proteins.

Once the transacting factor is identified, modulation of its binding to or regulation of expression of DNase polypeptide can be pursued, beginning with, for example, screening for inhibitors against the binding of the transacting factor to the DNase protein of the present invention. Activation or repression of the inventive DNase proteins could then be achieved in animals by applying the transacting factor (or its inhibitor) or the gene encoding it, e.g. in an expression vector. In addition, if the active form of the transacting factor is a dimer, dominant-negative mutants of the transacting factor could be made in order to inhibit its activity.

Furthermore, upon identification of the transacting factor, further components in the pathway leading to activation (e.g. signal transduction) or repression of a gene involved in the control of the inventive tumour associated polypeptide then can be identified. Modulation of the activities of these components can then be pursued, in order to develop additional drugs and methods for modulating the metabolism of protein degradation in animals. Thus, the present invention also relates to the use of the two-hybrid system as defined above for the identification of the inventive tumour associated polypeptide or activators or inhibitors of the inventive DNase polypeptide.

The compounds isolated by the above methods also serve as lead compounds for the development of analogue compounds. The analogues should have a stabilized electronic configuration and molecular conformation that allows key functional groups to be presented to the DNase polypeptide or its possible receptor in substantially the same way as the lead compound. In particular, the analogue compounds have spatial electronic properties which are comparable to the binding region, but can be smaller molecules than the lead compound, frequently having a molecular weight below about 2 kD and preferably below about 1 kD.

Identification of analogue compounds can be performed through use of techniques such as selfconsistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA.

Furthermore, said derivatives and analogues can be tested for their effects according to methods known in the art; see also supra. Furthermore, peptidomimetics and/or computer aided design of appropriate derivatives and analogues can be used, for example, according to the methods described above.

In a preferred embodiment of the above-described methods of the invention said cell is a cell of or, obtained by a method of the invention or is comprised in the above-described transgenic non-human animal.

Once the described compound has been identified and obtained, it is preferably provided in a therapeutically acceptable form.

It must be understood, that the compounds and methods as disclosed throughout this text are applicable to any mammalian individual. Thus the compounds and methods may be applied to animals as well as to human beings and are such useful in veterinary medical as in medical purposes. Animals, that may be of especial interest with respect to the present invention are companion animals, such as cats, dogs, etc. animals of agricultural interest such as cows, pigs, horses, laboratory animals such as rats, mice, hamsters, rabbits etc. and any other animal, that may be affected by a disorder characterized by abnormal growth of cells.

The present invention provides compounds and methods useful for detection and treatment carcinomas and their precursor lesions. In one aspect the present invention provides a method for the detection of carcinomas and their precursor lesions based on the determination of the presence or absence and/or the level of expression of DNase molecules in biological samples. This detection method may e.g. be employed in the course of early detection of neoplasias and precursory stages of tumours. In a second aspect the present invention provides a method for treatment of carcinomas and their precursor lesions by modulation of DNase gene products as therapeutically active agents. The invention also provides for therapeutic methods based on the modulation of the activity of DNase polypeptides. It is one aspect of the invention to provide a method for rational tumour management based on the detection of DNase gene products in patient samples and the tailoring of a therapy correlated to the detected over expression of said DNase gene products. Furthermore the present invention provides for a research or diagnostic test kit for performing the reactions involved in the detection of the presence or absence and/or the level of over expression of DNase genes. Finally the present invention relates to pharmaceutical compositions applicable in the treatment of carcinomas and their precursor lesions comprising DNase compounds as disclosed herein.

The following examples are given for the purpose of illustration only and are not intended to limit the scope of the invention disclosed herein.

Example 1

Immunochemical Detection of the Overexpression of DNase X in Tissue Samples of Carcinomas Sections of formalin fixed, paraffin embedded tissue samples of the colon were immunocytochemically stained using antibodies specific for DNase X.

The sections were rehydrated through incubation in xylene and graded ethanol, and transferred to Aqua bidest. Antigen Retrieval was carried out with 10 mM citrate buffer (pH 6.0) Therefore the slides were heated in a waterbath for 40 min at 95° C. The slides were cooled down to RT for 20 minutes, transferred to washing buffer (PBS/0.1% Tween20).

For inactivation of endogenous peroxidase the samples are incubated with 3% H2O2 for 20 min at RT and afterwards washed in PBS/0.1% Tween20 for 5 to 10 min.

The slides were then incubated with the primary antibody, rat anti-DNase X (1:25) (for 1 hour at RT, the slides were then rinsed with washing buffer and placed in a fresh buffer bath for 5 min. The antibody employed is directed against the peptide sequence (SEQ ID NO:3)
c a s l t k k r l d k l e l r t e p g f of human DNase X.

Afterwards the slides were incubated with the secondary antibody (goat anti rat (1:500)). Washing was performed 3 times for 5 minutes. Excess buffer was tapped off and the specimen was covered with 100 μl of visualization reagent for 30 min at RT. Slides were washed as before, and covered with 200 μl substrate-chromogen solution (DAB) for 10 min. Then slides were washed as before and counterstained for 3 min in a bath of haematoxylin. Residual haematoxylin was rinsed with distilled water, and specimens were mounted and coverslipped with an aqueous mounting medium.

The microscopic examination of the slides reveals, that cells immunoreactive with DNase X can be found in samples, that may microscopically be identified as samples of colorectal carcinoma. In carcinomas the DNase X specific staining is concentrated in the cellular nucleus. In contrast in control samples very few single cells may be stained. In all non-cancerous cells the staining is cytoplasmatic, whereas in cells of carcinomas and their precursor lesions the staining is located nuclear. Especially in gastrointestinal tissues endocrine cells show cytoplasmatic staining for DNase X. No other cells in gastrointestinal tissues may be stained. In other tested tissues there is no positive staining. In these cases the staining is localized in the cytoplasm of the cells.

The above described immunohistochemical staining procedure was furthermore applied to tissues from breast-, lung-, cervical-(CINIII), gastric-, oesophageal-, endometrial-, ovarian-carcinomas. In all these cases nuclear staining for DNase X could be observed in the cancerous cells. In normal tissue few to no staining was identified.

Moreover metastases from colorectal carcinoma located in the liver were analysed by immunochemical procedures as described above. The result showed nuclear staining in the tumour cells and no staining in the surrounding normal tissue.

Immunochemical analysis of peripheral venous blood, of bone marrow and of lymphocytes by the described methods revealed no immunoreactivity for DNase X in samples obtained from normal control individuals. This indicates, that disseminated tumour cells that are immunoreactive with DNase X might be identified in these samples by specific immunochemical staining with antibodies directed against DNase X.

The results show, that the staining with reagents specific for DNase X allows to identify carcinomas in biological samples. In carcinomas and their precursor lesions there is nuclear staining for DNase X with the employed antibody, whereas in normal tissue only few cells may be stained in the cytoplasm.

Generally it may be stated that staining is concentrated in the nucleus of the cells. However cytoplasmic immunoreactivity may also be seen in transformed cells (tumor tissue).

Example 2

Detection of disseminated tumour cells in lymph nodes of individuals Lymph node samples of patients obtained in the course of surgical resection of adenocarcinomas of the colon were employed to determine the presence of cells showing immunoreactivity with DNase X specific binding agents. In total samples from 7 patients with colon-carcinomas were included.

Immunohistochemical staining was performed as given in Example 1.

The experiment reveals that staining with the antibody directed against DNase X may be detected in samples of patients with carcinoma.

An immuno-histochemical staining for DNase X in the samples could improve the detectability of the disseminated tumour cells in the lymph tissue.

Example 3

Early Diagnosis of Ductal Carcinoma In Situ by Detection of DNase X in Cells Contained in Ductal Lavage Fluid A collective of 14 individuals was included in this study. 7 patients were identified as having calcifications in breast ducts indicative of early stage ductal carcinoma in situ by mammographic examination. 7 individuals did not show any signs indicating a neoplastic lesion of the breast.

Ductal lavages were performed with all 14 individuals and cells were isolated from the lavage fluid.

Cytological preparations were done from the lavages fluids by ThinPrep™ technology. Immunochemical staining was performed as described in Example 1.

The experiment reveals the presence of cells immunoreactive for DNase X in the cytological preparation of 9 individuals. In the samples of all patients with a mammographic diagnosis indicating the presence of ductal carcinoma in situ, cells immunoreactive for DNase X could be identified.

The result shows, that the conventional methods for identification of early stages of neoplasias of the breast may be improved by methods based on the detection of the DNase X immunoreactivity presented herein.

Example 4

Diagnosis of Gastrointestinal Carcinomas In Situ by Detection of DNase Activity in Body Fluids Using a monoclonal antibody directed against the DNaseX protein an overexpression of the DNaseX protein has been detected in every tumor entity which was analysed by immunohistochemistry. Therefore the overexpression of the DNaseX protein represents a general phenomena in tumors. Since the DNaseX protein is a soluble protein with an intrinsic enzymatic activity, the overexpression found on immunohistochemistry level suggests that the overexpression of the DNaseX protein found in tumor cells could lead to an enhanced level of DNaseX protein or DNase activity in body fluids of tumor patients.

To test this hypothesis we first analysed if the overexpression of the DNaseX protein leads to an enhanced DNase activity in sera of tumor patients.

Serum from individuals with different carcinomas were used to find out, whether there is a correlation between diagnosis and DnaseX activity in the serum. In total serum samples from patients with liver carcinoma (one patient), liver metastases originating from colorectal cancer (7 patients), thyroid carcinoma (one patient), pancreatic carcinomas (7 patients), oesophageal carcinomas (4 patients), gastric carcinomas (17 patients), colorectal carcinomas (22 patients), rectal carcinomas (8 patients), colorectal adenomas (7 patients) and from 19 normal controls were included.

To measure the DNase activity in sera from tumor patients we used a DNase activity test established for the determination of reduced DNase activity levels in systemic lupus erythematosus (SLE) patients. Using this test we were able to detect an enhanced DNase activity in sera of tumor patients.

In the used DNase activity test the DNase present in serum leads to a degradation of the DNase substrate coated to the ELISA plate. Therefore the higher the DNase activity present in the serum the lower is the binding of the secondary antibody and the concomitant ELISA value (inverse relationship between signal height and DNase activity).

Figure 7:
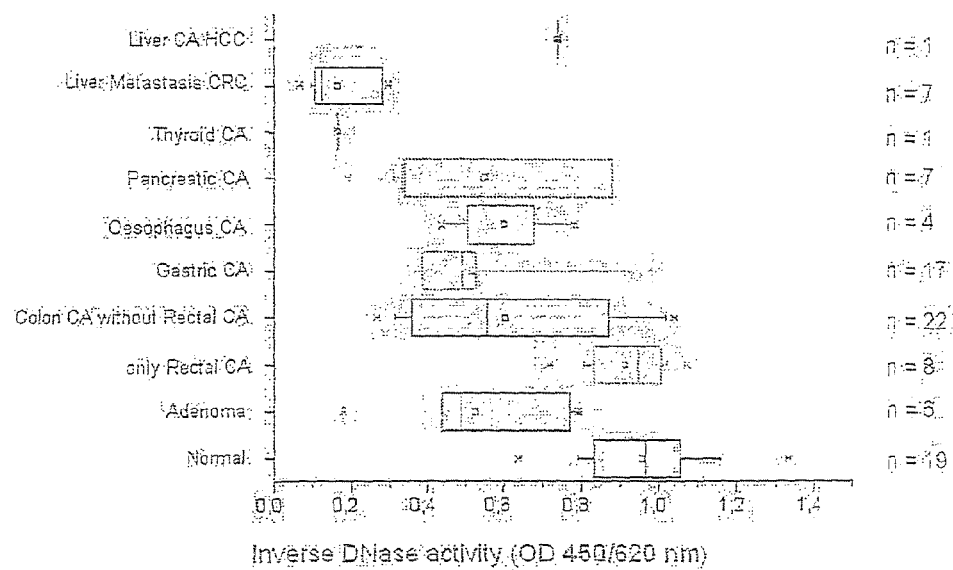
FIG. 7: Graph inversely showing DNase activities measured in serum of individuals with different kinds of carcinomas; the graph displays, that on average all carcinomas tested except for rectal carcinomas are accompanied by elevated serum DNase activity. (details in Example 4)

The results of the experiment are given in FIG. 7. Whereas sera of 8 rectal carcinomas do not show elevated (or only weakly elevated) DNase activity levels, most sera of colon carcinoma and adenoma patients do show elevated DNase activity levels. Also the pancreatic and the gastric cancer patients do show elevated DNase activity levels. Whereas a serum of a liver carcinoma patient does not show an elevated DNase activity level, all 7 liver metastasis sera do show extremely elevated DNase activity levels.

Immunohistochemical analysis demonstrated an overexpression of the DNaseX protein in more than 95% of bladder carcinomas. A DNase activity test with urine from bladder carcinoma patients revealed an enhanced DNase activity in patient's urine compared to urine from healthy controls (not shown).

In addition to the detection of elevated levels of DNase based on the enzymatic detection, we also performed standard ELISA experiments with a combination of capture and detection antibody directed against DNaseX. A combination of a monoclonal antibody directed against DNaseX and a polyclonal antibody directed against DNaseX revealed the most specific results in respect of sensitivity and specificity of the test. Using this test an enhanced level of DNaseX protein has been detected in body fluids like serum, sputum and urine of tumor patients (not shown).

Based on the overexpression of the DNaseX protein in tumors screening tests can be efficiently performed which lead to the identification of patients with yet unrecognized tumors. Therefore the time point of detection is much earlier compared to standard tests like hemeoccult (fecal occult blood) test. In addition tumor types can now be detected which are until now extremely difficult to detect like gastric cancer or pancreas cancer. Since this cancer early detection test is able to identify almost all or all tumor entities the test fulfils an important criteria for a general and cheap early cancer test for a mass screening.

What is claimed is:

1. A method for detection of carcinomas or their precursor lesions comprising:
   a) obtaining a biological test sample from a human;
   b) binding in the test sample an antibody that specifically binds to peptide sequence SEQ ID NO: 3 of human DNase-X polypeptide or an antigen binding fragment thereof to determine the level of peptide comprising sequence SEQ ID NO: 3 in the test sample;
   c) comparing the level of peptide comprising sequence SEQ ID NO: 3 of human DNase-X polypeptide within said test sample to the level of peptide comprising sequence SEQ ID NO: 3 of human DNase-X polypeptide within a corresponding control sample; and
   d) classifying a test sample exhibiting an increased level of peptide comprising sequence SEQ ID NO: 3 of human DNase-X polypeptide relative to the level of peptide comprising sequence SEQ ID NO: 3 of human DNase-X polypeptide in the control sample as indicative of the presence of a carcinoma or precursor lesion,
   wherein the carcinoma is a colon, breast, lung, cervical, gastric, esophageal, endometrial, ovarian, or bladder carcinoma, and
   wherein the precursor lesion is a precursor lesion for colon carcinoma or breast carcinoma.

2. The method according to claim 1, wherein the test sample is blood, plasma, serum, liquor, lymph, bone marrow, swabs, washes, lavages, secretions, transudates, exudates, sputum, stool, urine, semen, cell- and tissue-samples, or biopsies.

3. The method according to 1, wherein at least one antibody that specifically binds to the peptide sequence SEQ ID NO: 3 of human DNase-X polypeptide or antigen binding fragment thereof is detectably labeled.

4. The method according to claim 3, wherein the label is selected from the group consisting of a radioisotope, a bioluminescent compound, a chemiluminescent compound, a fluorescent compound, a metal chelate, a biological binding structure and an enzyme.

5. The method according to claim 3, wherein an immunocytochemical detection procedure is carried out on the detectably labeled antibody.

6. The method according to claim 4, wherein the biological binding structure is biotin or digoxygenin.

* * * * *